US00RE37926E

(19) United States
(12) Reissued Patent
Fujita et al.

(10) Patent Number: US RE37,926 E
(45) Date of Reissued Patent: Dec. 10, 2002

(54) APPARATUS AND METHOD FOR DETECTING TRANSPARENT SUBSTANCES

(75) Inventors: Toshihiro Fujita, Osaka (JP); Ikkan Nishihara, Osaka (JP); Takeshi Takao, Osaka (JP); Shoji Fujii, Osaka (JP); Takaaki Douko, Osaka (JP); Tatsumi Tamon, Osaka (JP); Kimiyasu Kurita, Osaka (JP); Katsuhiro Shoji, Osaka (JP)

(73) Assignee: Idec Izumi Corporation, Osaka (JP)

(21) Appl. No.: 09/568,938

(22) PCT Filed: Feb. 19, 1997

(86) PCT No.: PCT/JP97/00461

§ 371 (c)(1),
(2), (4) Date: Oct. 21, 1997

(87) PCT Pub. No.: WO97/31384

PCT Pub. Date: Aug. 28, 1997

Related U.S. Patent Documents

Reissue of:
(64) Patent No.: 6,043,504
Issued: Mar. 28, 2000
Appl. No.: 08/945,428
Filed: Feb. 19, 1997

(30) Foreign Application Priority Data

Feb. 21, 1996 (JP) ..... 8-033658
Apr. 15, 1996 (JP) ..... 8-092582

(51) Int. Cl.[7] ..... G01N 15/06
(52) U.S. Cl. ..... 250/573; 250/339.12
(58) Field of Search ..... 250/573, 576, 250/577, 223 B, 339.12, 341.1; 356/339, 442

(56) References Cited

U.S. PATENT DOCUMENTS 4,281,245 A * 7/1981 Brogardh et al. ..... 250/227.23
4,514,860 A * 4/1985 Adolfsson et al. ..... 250/226
4,567,366 A 1/1986 Shinohara ..... 250/339
4,823,008 A * 4/1989 Sturm ..... 250/341.1
4,947,036 A * 8/1990 Pokorski et al. ..... 250/226
5,112,124 A * 5/1992 Harjunmaa et al. ..... 356/39
5,222,810 A * 6/1993 Kleinerman ..... 250/227.23
5,903,006 A * 5/1999 Kiuchi et al. ..... 250/339.12

FOREIGN PATENT DOCUMENTS

| | | |
|---|---|---|
| EP | 0273433 | 7/1988 |
| EP | 0329083 | 8/1989 |
| EP | 0340443 | 11/1989 |
| GB | 2110819 | 6/1983 |
| JP | 5641239 | 9/1981 |
| JP | 57192842 | 11/1982 |
| JP | 58143242 | 8/1983 |
| JP | 6134424 | 2/1986 |

(List continued on next page.)

*Primary Examiner*—Que T. Le
(74) *Attorney, Agent, or Firm*—Ostrolenk Faber Gerb & Soffen

(57) ABSTRACT

A semiconductor light-emitting device which emits first light of a wavelength absorbed by a substance containing an OH group is sent toward a detection object. A semiconductor light-emitting device emits second visible light toward the detection object. A photoreceptor receives light from the detection object and acquires first and second received light-quantities derived from the respective ones of the first and second light. A processing system corrects the first photoreceiving quantity on the basis of the second photoreceiving quantity. The processing system determines the color of the detection object by the second photoreceiving quantity, and corrects the first photoreceiving quantity on the basis of this determination result. Further, it compares the corrected first photoreceiving quantity with a prescribed threshold value, detects whether or not water, which is the subject containing the OH group, is contained in the detection object, and outputs the same as an output signal.

22 Claims, 22 Drawing Sheets

FOREIGN PATENT DOCUMENTS

| | | | |
|---|---|---|---|
| JP | 62286317 | | 12/1987 |
| JP | 1262441 | | 10/1989 |
| JP | 220934 | | 5/1990 |
| JP | 220936 | | 5/1990 |
| JP | 2-126437 | * | 10/1990 |
| JP | 4151546 | | 5/1992 |
| JP | 4204354 | | 7/1992 |
| JP | 5005651 | | 1/1993 |
| JP | 599845 | | 4/1993 |
| JP | 6-164690 | * | 6/1993 |
| JP | 7113745 | | 5/1995 |
| JP | 7-294428 | * | 11/1995 |
| WO | 94 08226 | * | 4/1994 |

* cited by examiner

APPARATUS AND METHOD FOR DETECTING TRANSPARENT SUBSTANCES

Matter enclosed in heavy brackets [ ] appears in the original patent but forms no part of this reissue specification; matter printed in italics indicates the additions made by reissue.

TECHNICAL FIELD

The present invention relates to a switching device utilizing photoelectric conversion used in an automation line of a factory or the like.

BACKGROUND TECHNIQUE

While various sensors are used in an automation line of a factory for process control or the like, a photoelectric switch providing a photoelectric sensor with a switching function is employed for various uses since the same has such an advantage that detection of an object can be performed in a non-contact manner.

A reflection type conventional photoelectric switch is adapted to project light from a projector toward a detecting position and detect presence/absence of reflected light from the detecting position by a photoreceptor, thereby recognizing whether or not a detection object is present on the detecting position. On the other hand, a transmission type switch oppositely arranges a projector and a photoreceptor and utilizes the fact that no light reaches the photoreceptor by shading by a detection object if the same is present in a space therebetween, and is formed as the so-called photo-interruptor. In either case of these, it performs opening/closing of a required switch in response to a photoreceiving state of the photoreceptor, thereby serving a function as a photoelectric switch.

However, since such a conventional photoelectric switch is on condition of light reflectivity or shadingness of the object, as to a detection object which is poor in such an optical property, particularly a transparent or semitransparent liquid or solid (hereinafter "substance having transparency") its detection is difficult. Namely, since the light from the projector is hardly reflected or shaded in case of such a substance having transparency, a photoreceiving output of the photoreceptor hardly changes by presence/absence of the detection object in the conventional photoelectric switch. Further, while a threshold level for discriminating the photoreceiving output of the photoreceptor must be set in the vicinity of a zero level in order to forcibly detect slight reflection or shading, it comes to that switching of ON/OFF takes place only by small disturbance such as noise when doing so, and this causes wrong information.

On the other hand, every substance is not completely transparent with respect to all wavelengths, but has light absorbance depending on the wavelength of light, as is generally known. In correspondence to this, there is proposed a technique of extracting a specific wavelength by passing light from a white light source through a filter, projecting it to an object, and performing presence/absence detection of the object or the like in response to the absorbance of the light passing through the object.

However, a transmission waveband readily available as a filter does not necessarily coincide with the light absorption waveband of the object to be detected in this case. Therefore, it often happens that detection sensitivity does not reach a necessary level in practice.

Further, an incandescent lamp used as the white light source has a large size, and hence an optical system for projecting this to the object also increases in size. Therefore, the size of the projector which must contain these components increases.

Under such circumstances, a light absorption utilization type photoelectric detector employing a white light source and a filter is limited in its use, and it is difficult to employ the same for an apparatus such as a photoelectric switch which is miniature and used generically.

Further, it is difficult to obtain a complete filter transmitting light of only a noted wavelength by such a technique, and light other than the wavelength is considerably transmitted through the filter in the actual situation. Therefore, it is difficult to project only light of a specific wavelength responsive to absorptivity of the object, and it often happens that a number of wavelengths are mixed in the detection. Thus, influence of absorption as to other than the noted wavelength is unavoidable, and there are some cases that detection of the object becomes incorrect.

Thus, detection of a detection object which is poor in optical property with light in a non-contact manner has various problems, while there is also a problem that a larger number of other sensors must be mounted in problem order to mount one sensor. In particular, photoelectric switches are utilized for various uses, and hence a number of similar photoelectric switches are arranged/disposed on a single automation line in the actual situation.

Even for a detecting operation of merely detecting the quantity of a liquid in a container, for example, it comes to that photoelectric switches performing two types of detection as to whether or not the container has reached an injecting position and whether or not the injection quantity is proper in the automation line.

Thus, a wide installation space is necessary for a number of photoelectric switches in the actual automation line, and much time is required for installing these many photoelectric switches in case of manufacturing the automation line itself.

Incidentally, the automation line of a factory is shifting to multi-type small-lot production in recent years, such that products having various shapes, colors and the like generally flow on the same line. In order to cope with such circumstances, it has become necessary to install a larger number of sensors responsive to conditions on the line with respect to products of various different conditions despite the same or similar objects. This is because the conventional photoelectric switch has been so designed that the same can perform only one type detection under one condition and hence various types of photoelectric switches responsive to various detection objects are required.

As hereinabove described, the photoelectric switch has such excellent utility value that the same can detect a detection object in a non-contact manner, and it can be said that enlargement of its use and convenience is important in future research and development.

DISCLOSURE OF THE INVENTION

<Object of the Invention>

The present invention has been proposed in consideration of such circumstances, and a first object is to provide a photoelectric switch which can detect substances having transparency, i.e., (1) a substance containing an OH group, and (2) a substance containing a $CH_2$ group or a $CH_3$ group as objects and performs detection thereof in excellent accuracy, is formed by elements easy to obtain, can be structured in miniature, and has high generality.

A second object is to provide a photoelectric switch capable of a plurality of types of detection on the same detecting position.

<Summary of the Invention>

The present invention is directed to a photoelectric switching device irradiating a detection object with light and receiving light from the detection object thereby generating a detection signal.

The present invention comprises a semiconductor light-emitting device generating light of a wavelength selected from a range of 1.40 μm to 1.50 μm applied to the said detection object, a semiconductor photoreceptor generating an output value responsive to a received light-quantity derived from the applied light in light from the detection object, and compare means comparing the output value with a prescribed threshold value for generating a detection signal.

Further, the present invention comprises a semiconductor light-emitting device generating light of a wavelength selected from a range of 1.60 μm to 1.80 μm applied to the said detection object, a semiconductor photoreceptor generating an output value responsive to a received light-quantity derived from the applied light in light from the detection object, and compare means comparing the output value with a prescribed threshold value for generating a detection signal.

According to the present invention, a readily obtainable semiconductor light-emitting device generating light of a wavelength responsive to a specific absorption waveband of a substance containing an OH group or a $CH_2$ group and/or a $CH_3$ group, is utilized. In this way a photoelectric switching device is realized which does not have to use a filter or a large optical system, and is capable of miniaturization and is high in generality. Further, the waveband width of the emission wavelength of the semiconductor light-emitting device is sufficiently narrow, whereby influence of a wavelength other than a required wavelength is small, and accuracy in detection of the object is high. Thus, a photoelectric switch is produced whose effectivity in an automation line of a factory or the like is particularly high.

Further, the present invention comprises light-emitting means generating light of a plurality of different wavelengths toward a detection object, photoreceiving means generating a plurality of output values responsive to received light-quantities derived from respective ones of the light of a plurality of different wavelengths in light from the detection object, and detection signal generation means generating a detection signal on the basis of the plurality of output values.

According to the present invention, a plurality of types of detection can be quickly correctly performed in an automation line of a factory or the like. Further, it is not necessary to install a plurality of photoelectric switching devices, the step of installation is reduced while delay processing of operation timing becomes unnecessary, and equipment design is simplified.

In one mode of the present invention, the light of the plurality of wavelengths is light of two different wavelengths, and it is rendered possible to precisely cope with types of diversified detection objects by correcting output values derived from the light of two different wavelengths in the detection signal generation means.

In a preferred embodiment of the present invention, water is detected as a typical substance containing an OH group. Further, alcohol or acrylic resin is detected as a typical substance containing a $CH_2$ group or a $CH_3$ group.

In another preferred embodiment of the present invention, colors of detection objects are determined, and then whether or not detection objects of different colors contain water is correctly detected.

In still another preferred embodiment, detection of presence of a detection object and a surface state of the detection object are implemented by a single photoelectric switching device without performing delay processing.

Other objects and features of the present invention are clarified in the following description.

BEST MODES FOR CARRYING OUT THE INVENTION

The present invention spreads utilization modes of a photoelectric switching device which has been generally employed in an automation line of a factory or the like, while principle modes thereof can be roughly classified into a photoelectric switching device detecting a specific substance by employing a specific wavelength, and a photoelectric switching device performing a plurality of types of detection from a detection object by employing light of a plurality of different wavelengths.

In the following, preferred embodiments are described for every one of these classifications.

<1. Photoelectric Switch Utilizing Light of Specific Wavelength>

<1.1 Principle of the Invention>

Before explaining concrete structures of the embodiments of the present invention, description is now made as to an employment reason for a waveband in the present invention, and a waveband implemented in a semiconductor light-emitting device.

<1.1.1 Relations between the Invention and Light Absorption Characteristics of Various Types of Substances>

One of photoelectric switches utilizing light of a specific wavelength according to the present invention is based on a principle of utilization of a specific absorption spectrum of an OH group, and employs a 1.4 $\mu$m band (1.40 to 1.50 $\mu$m) as an emission wavelength responsive to this absorption waveband.

Further, another one of photoelectric switches utilizing light of a specific wavelength is based on a principle of utilization of a specific absorption spectrum of a $CH_2$ group and/or a $CH_3$ group.

FIG. 1 to FIG. 8 show measured results serving as the basis of selection of such wavebands. The axes of ordinates of these graphs are light transmittance (0% to 100%), and the axes of abscissas are wavelengths (unit $\mu$m). Therefore, troughs of the graphs correspond to absorption peaks. While there are parts where upper limits slightly exceed 100%, this results from errors. Substances provided with (*) marks in lower sections of these FIG. 1 to FIG. 8 are substances containing $CH_2$ groups or $CH_3$ groups, and others are substances containing OH groups.

Figure 1:
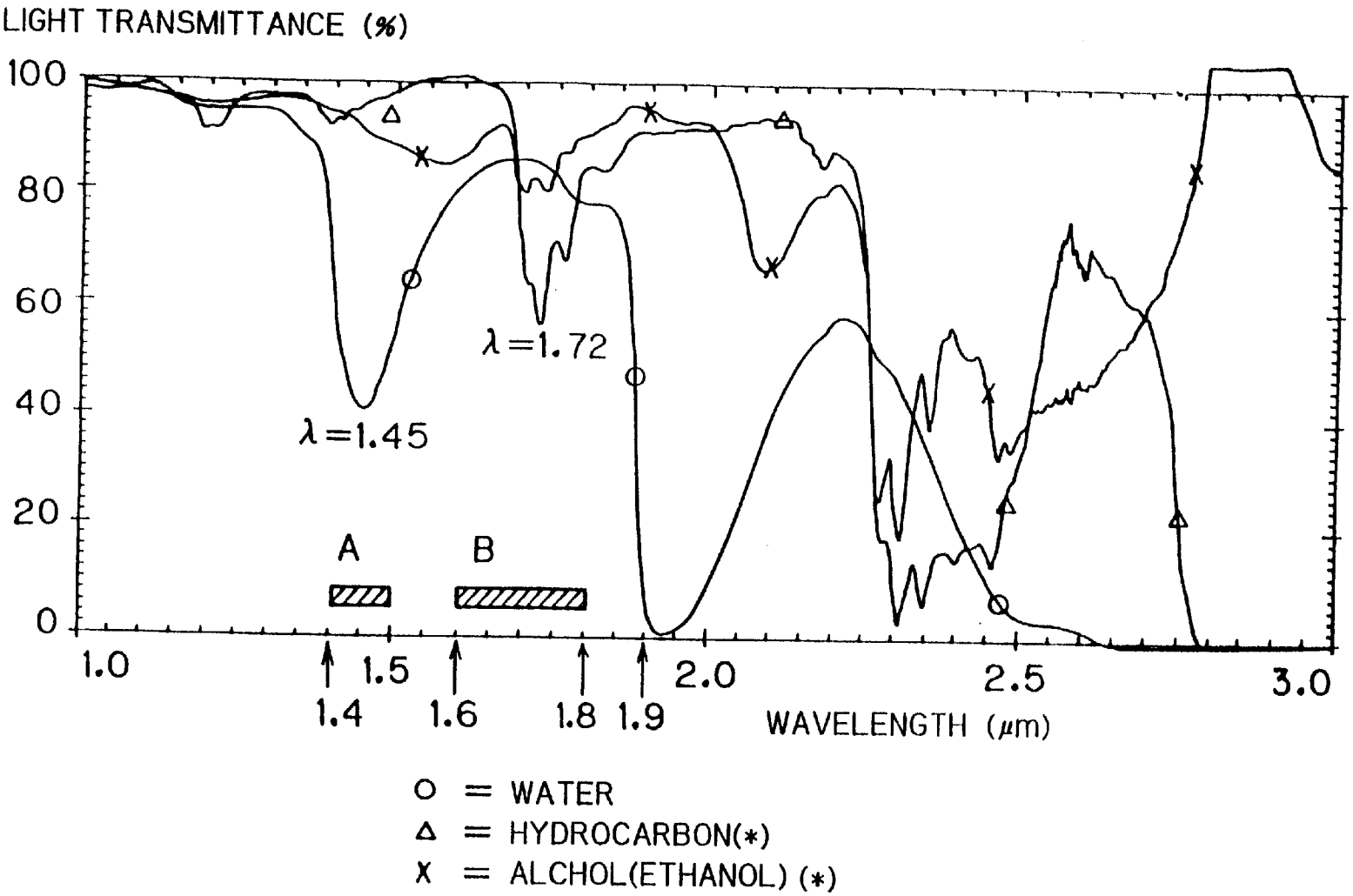
FIG. 1 to FIG. 6 are graphs showing measured results of light transmission spectra as to various liquids.
Figure 2:
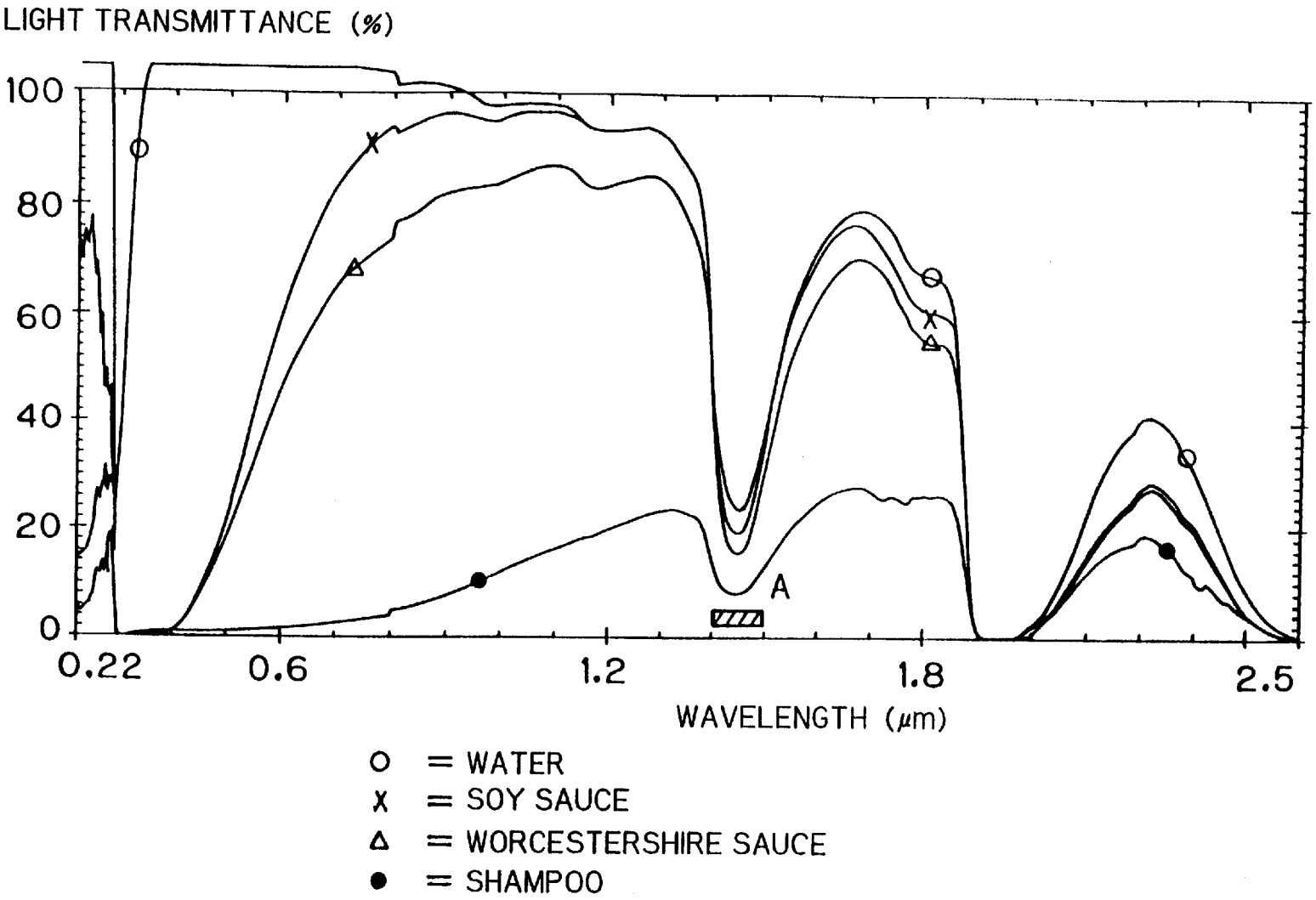
Figure 3:
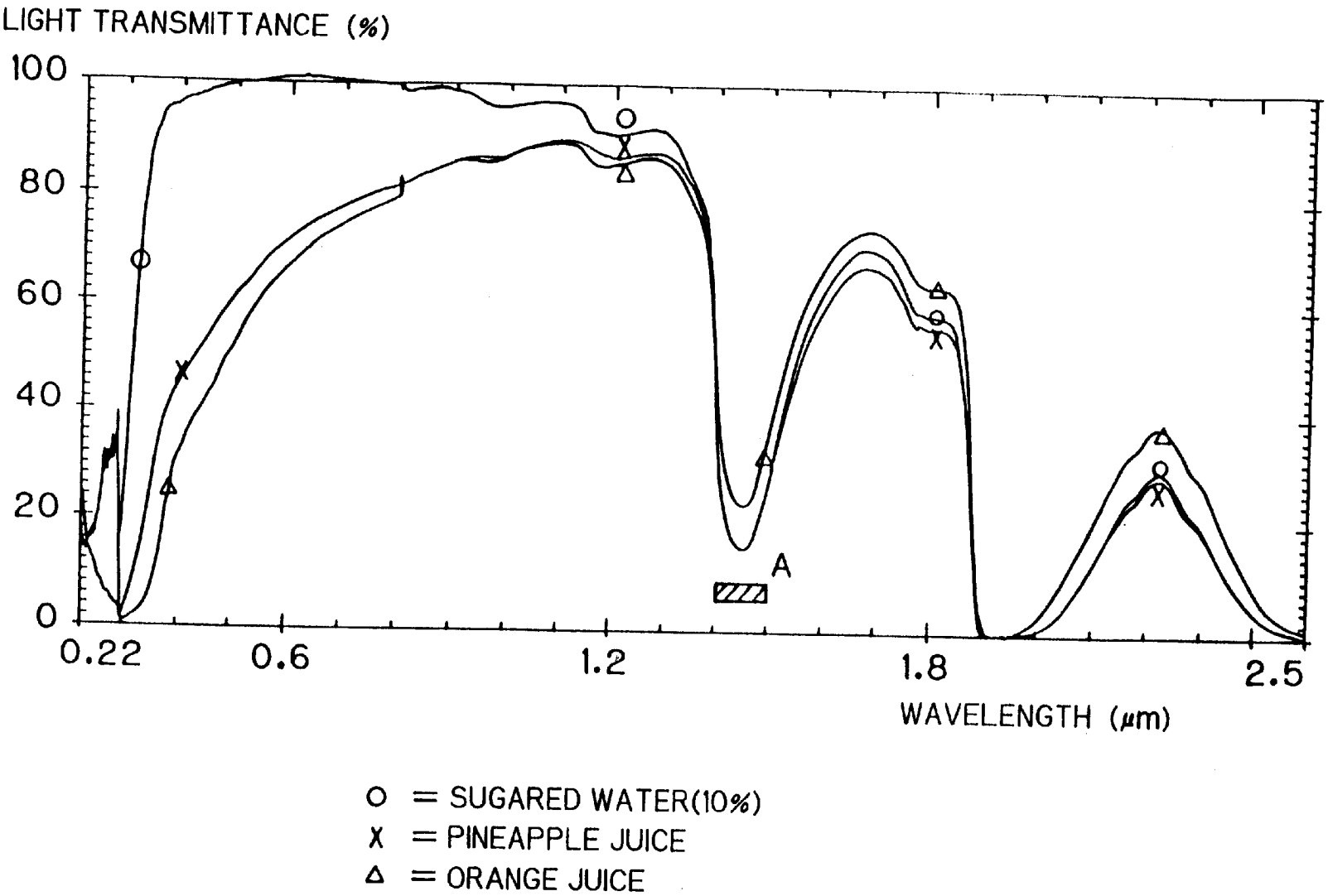
Figure 4:
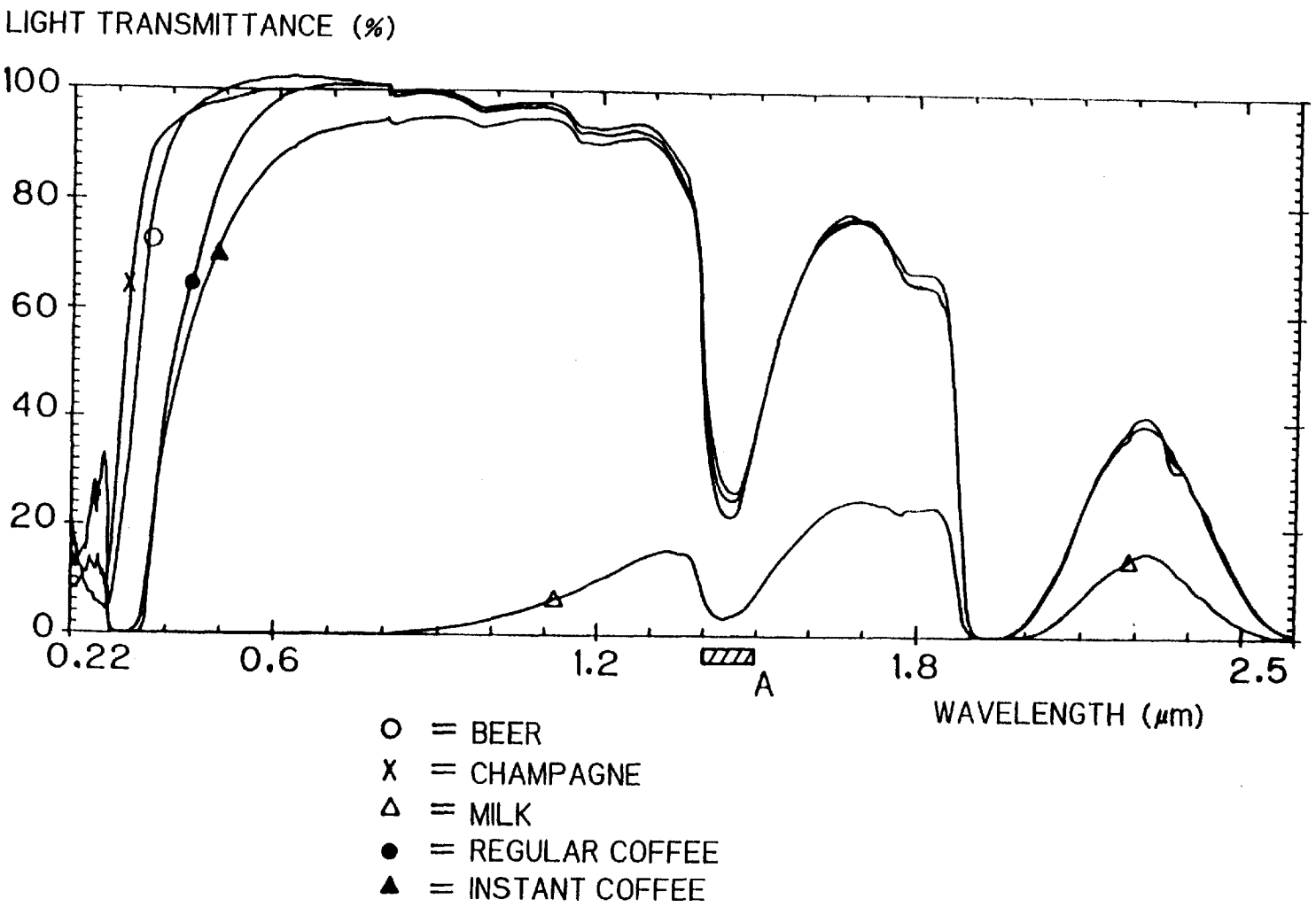
Figure 5:
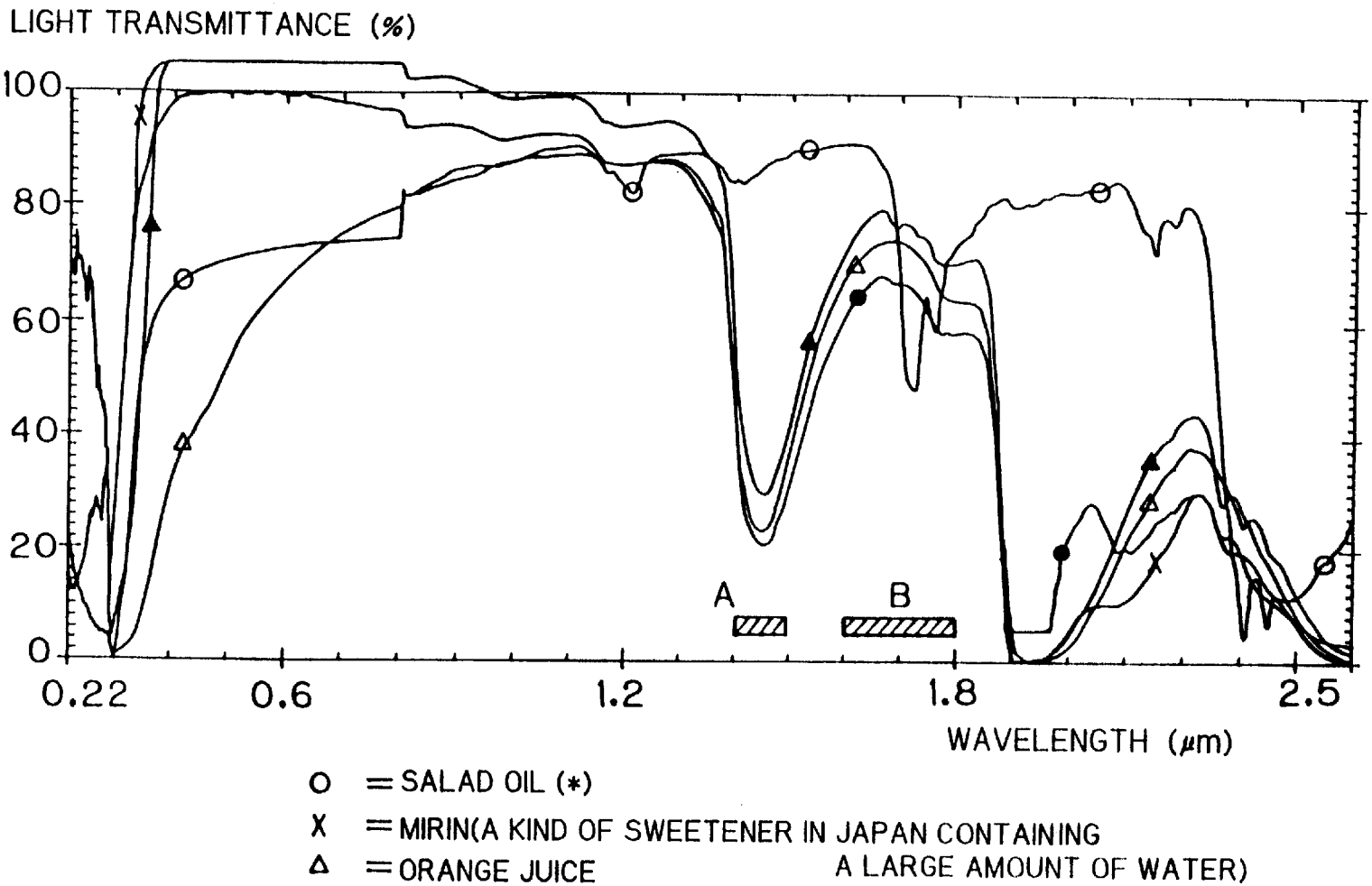
Figure 6:
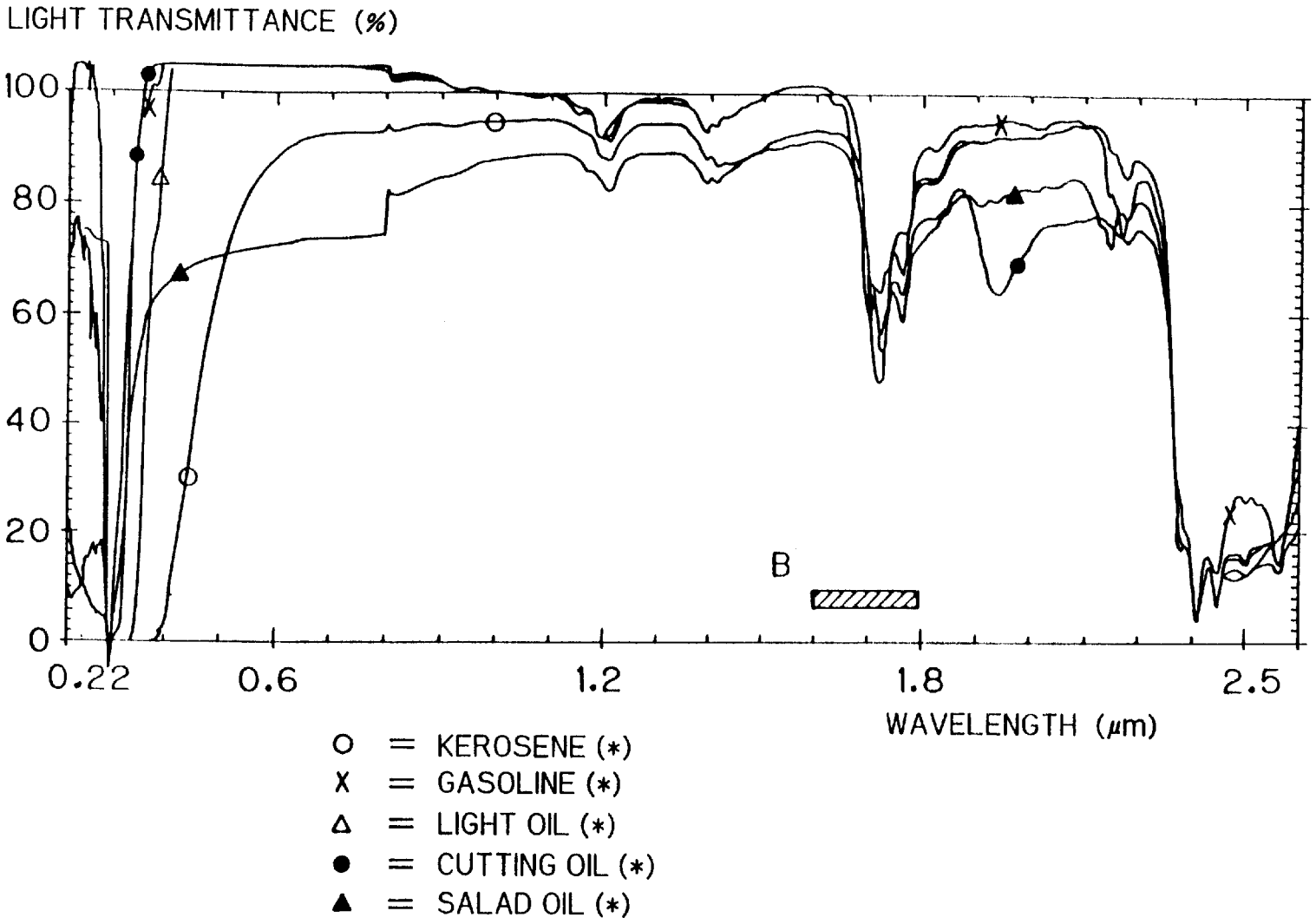

First, a measurement result of water ($H_2O$=H+OH) containing an OH group is noted in FIG. 1. As understood from this result, water has light absorption peaks in the vicinity of 1.45 $\mu$m and in the vicinity of 1.95 $\mu$m. While it is possible to obtain a photoelectric switch utilizing light absorption for whichever waveband of these is used, wavebands obtainable on industry as semiconductor light-emitting devices are limited to some extent in practice, and a 1.4 $\mu$m band (1.40 to 1.50 $\mu$m) is employed in the present invention. Referring to FIG. 1, this waveband is added as "A". An example of semiconductor light-emitting devices forming the premise of such selection is described later.

On the other hand, in hydrocarbon and ethyl alcohol (ethanol) serving as organic liquids containing $CH_2$ groups or $CH_3$ groups in FIG. 1, they have absorption peaks in the vicinity of 1.72 $\mu$m and the like. In consideration of the wavelengths of semiconductor light-emitting devices obtainable on industry similarly to water, the present invention employs a 1.6 to 1.7 $\mu$m band (1.60 to 1.80 $\mu$m). This waveband is added as "B" in FIG. 1.

FIG. 2 to FIG. 6 show results similar measurement performed as to other various substances (partially overlapping with the result included in FIG. 1). While the contents of these graphs are clear from the figures and hence not fully described here, it can be understood from these graphs that the substances containing OH groups as main components and the organic liquids containing $CH_2$ groups or $CH_3$ groups have absorption peaks in the vicinity of the 1.4 $\mu$m band A and in the vicinity of the 1.6 to 1.7 $\mu$m band B respectively.

Namely, the 1.4 $\mu$m band A is one of common absorption bands in various liquids containing OH groups, and the 1.6 to 1.7 $\mu$m band is one of common absorption bands in various organic liquids containing $CH_2$ groups or $CH_3$ groups.

Figure 7:
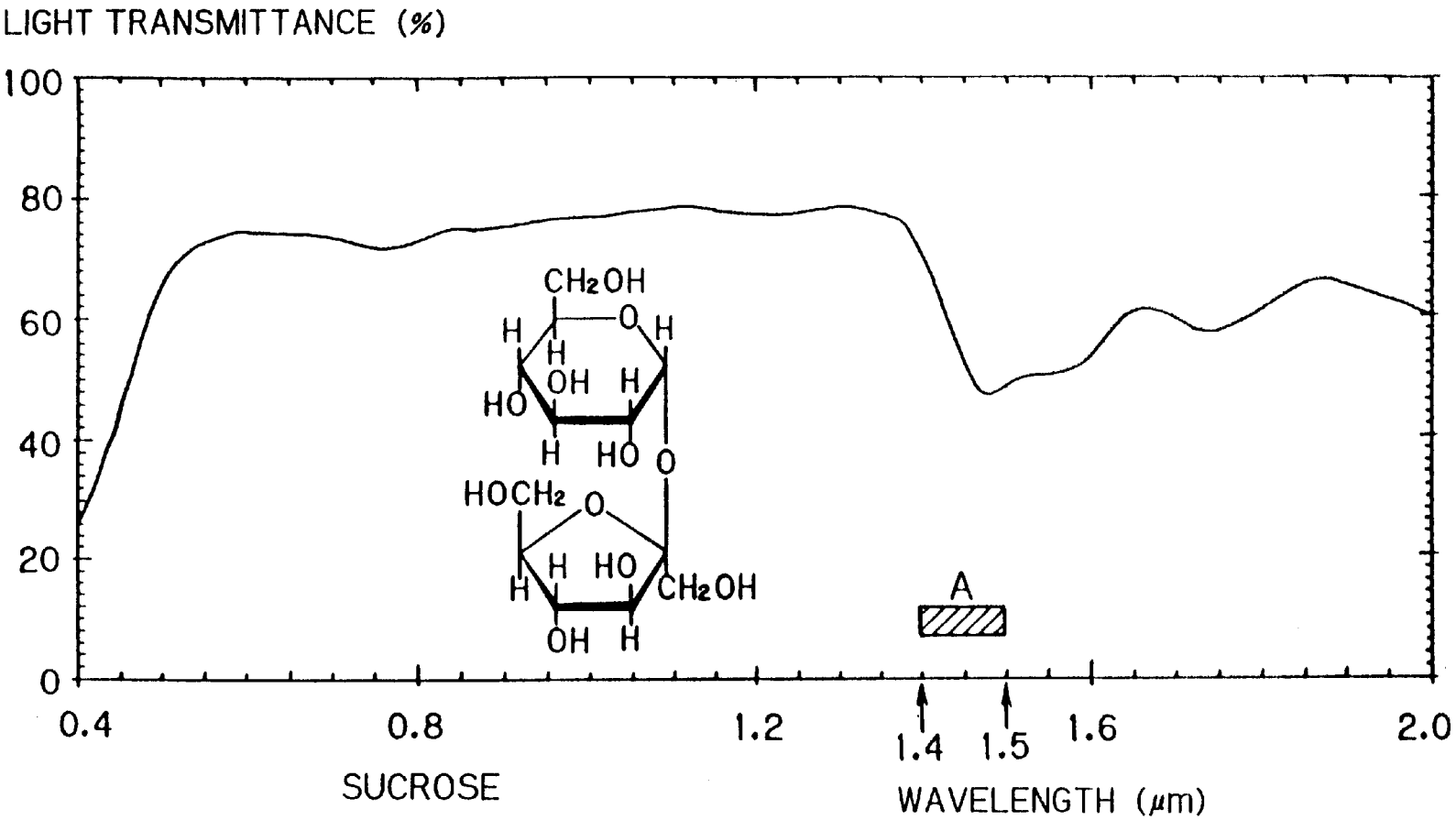
FIG. 7 is a graph showing a measured result of a light transmission spectrum as to sucrose which is a solid containing an OH group.
Figure 8:
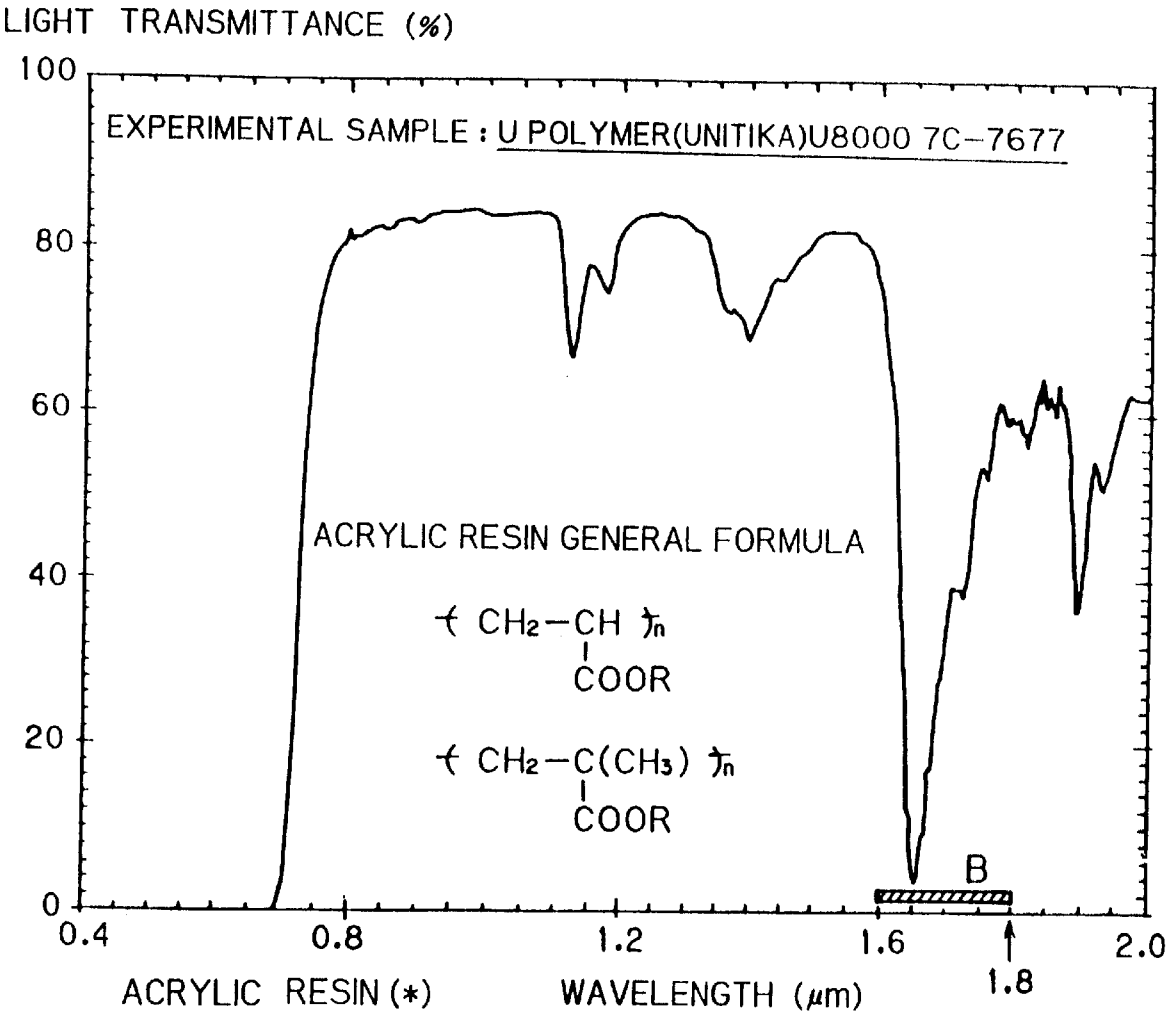
FIG. 8 is a graph showing a measured result of a light transmission spectrum as to acrylic resin which is a solid containing a $CH_2$ group or a $CH_3$ group.

Further, while these FIG. 1 to FIG. 6 are experimental results as to liquids, the present invention is also applicable as to solids. FIG. 7 is an experimental result of sucrose (cellulose or cane sugar) as an example of a solid containing an OH group, which has an absorption peak in the vicinity of the 1.4 $\mu$m band. Further, FIG. 8 is an experimental result of transparent plastic (concretely acrylic resin) as an example of a solid containing a $CH_2$ group or a $CH_3$ group, which has an absorption peak in the vicinity of the 1.6 to 1.7 $\mu$m band B.

Therefore, it is possible to obtain a photoelectric switch which is effective for detection of these substances by utilizing light absorption in these wavebands whether they are liquids or solids, and the present invention is based on such fact.

<1.1.2 Absorption Wavelength and Wavelength Selection for Every Detection Object>

Figure 9:
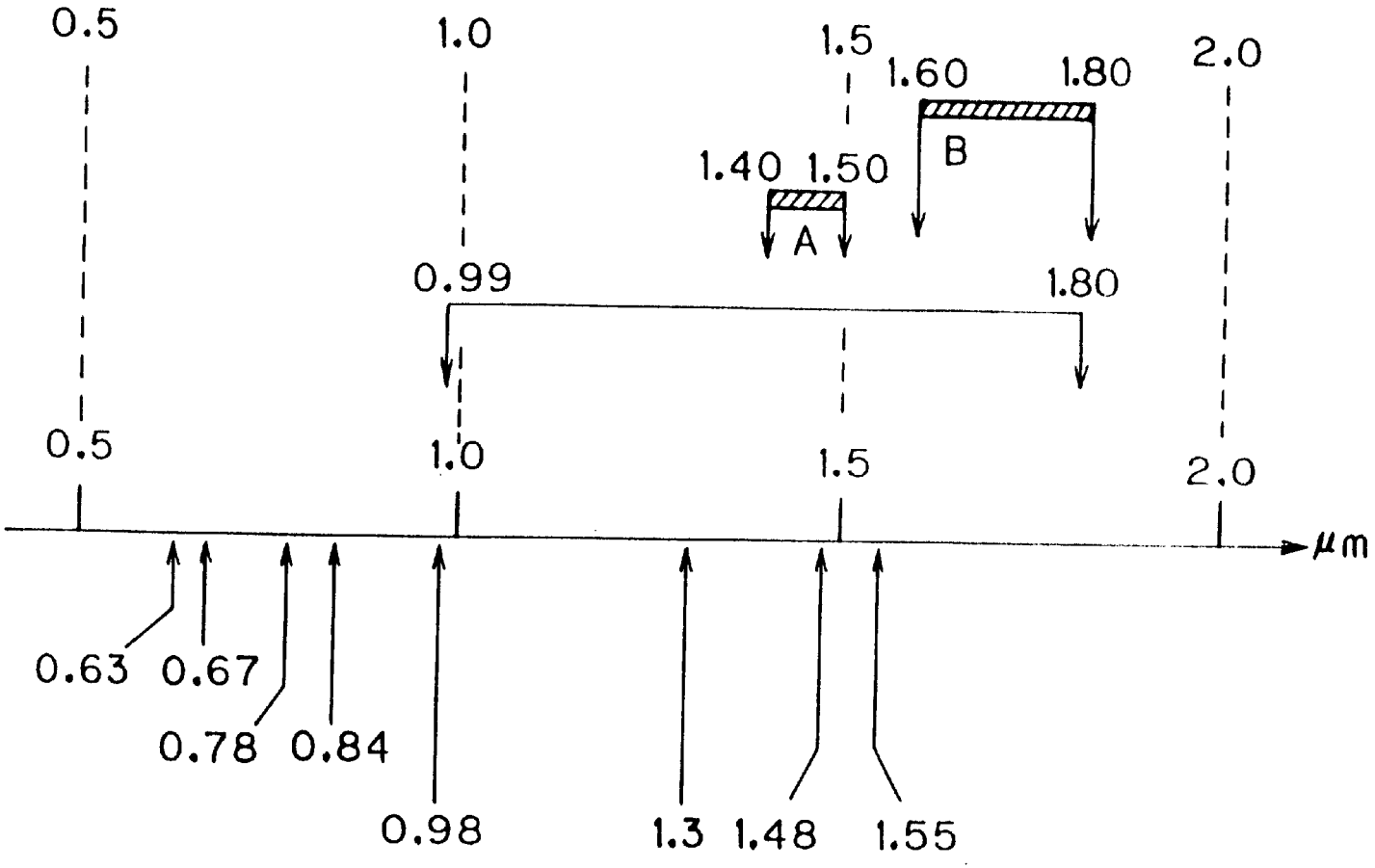
FIG. 9 is an explanatory diagram of wavebands employed in preferred embodiments of the present invention.

The ground as to why the 1.4 $\mu$m band (1.40 to 1.50 $\mu$m) and the 1.6 to 1.7 $\mu$m band (1.60 to 1.80 $\mu$m) have been particularly employed in the present invention among the absorption peaks determined from the aforementioned measured results of the absorption spectra is now described. Wavelength values and wavebands appearing in the following description are illustrated in FIG. 9, and this FIG. 9 would be also referred to.

<1.1.3 Details of Classification and Utilization of Semiconductor Light-emitting Devices by Emission Wavebands>

As to semiconductor light-emitting devices, particularly semiconductor lasers, those of various wavebands have been developed as generally known, and those wavelengths have been developed with objects for respective applications. Generally, these are divided into shorter wavebands and longer wavebands.

The shorter wavebands among these have been developed mainly for the so-called optical information processing such as optical disks represented by CDs, laser printers or sensors including photoelectric switches. There is a laser employing ban $Al_xGa_{1-x}As$ compound semiconductor as a typical one thereof, and wavelength 0.84 $\mu$m and 0.78 $\mu$m bands or the like, for example, can be implemented by adjusting a composition ratio x in this composition.

In optical disks or the like to which wavelength shortening is particularly required, a laser of an $(Al_xGa_{1-x})_yIn_{1-y}P$ system has been developed, and a 0.67 $\mu$m band and a 0.63 $\mu$m band have been implemented. Further, a laser employing a group II–VI compound semiconductor having large band gap energy such as ZnSe or ZnS has also been researched/developed for further wavelength shortening.

On the other hand, a longer waveband semiconductor laser has been developed with the principal object of application to an optical fiber communication system, and is created by mainly employing a compound semiconductor of an $In_{1-x}Ga_xAs_yP_{1-x}$ system. A wavelength used in optical communication or the like is a 1.3 $\mu$m band or a 1.55 $\mu$m band, for example. The reason why this waveband has been selected is for meeting such demands that an optical signal can be transmitted over a long distance with small propagation loss since there is small absorption in glass which is the material for optical fiber. In an optical fiber amplifier, a technique which can implement a gain of at least 30 dB with respect to an optical signal by employing a semiconductor laser of a wavelength 1.48 $\mu$m band or a 0.98 $\mu$m band as excitation light for fiber doping erbium (Er) of a rare earth element in optical fiber has been developed, and a laser of a 0.98 $\mu$m or 1.48 $\mu$m band which is a new waveband has been thereby developed.

Among the aforementioned shorter wavebands and longer wavebands, those becoming important in the present invention are the longer wavebands (refer to FIG. 9).

<1.1.4 Composition and Fabrication Corresponding to Emission Waveband>

Incidentally, compound semiconductors which are the materials for the aforementioned semiconductor lasers are formed by mixed crystals of a plurality of types of atoms. As to this, "Heterostructure Lasers", H. C. Casey, Jr. & M. B. Panish, Academic Press, 1978 is a bibliography widely known in this field, for example. According to this literature, the relation between an energy gap Eg (unit eV) between a valence band and a filled band of a direct transition type compound semiconductor and an emission wavelength λ (unit μm) is provided by:

$$Eg\ (eV)=1.2398/\lambda\ (\mu m)$$

Particularly in a mixed crystal semiconductor of $In_{1-x}Ga_xAs_yP_{1-y}$, a range which can be taken by its energy gap is controllable in the range of $0.73 \leqq Eg \leqq 1.25$ (eV) by changing composition ratios x and y in the ranges of $0 \leqq x \leqq 1$ and $0 \leqq y \leqq 1$. Therefore, the range of a light-emittable wavelength λ of $In_{1-x}Ga_xAs_yP_{1-y}$ is $0.99 \leqq \lambda \leqq 1.70$ (μm).

<1.1.5 Semiconductor Light-emitting Device Examples in the Invention>

Thus, the waveband currently obtainable in the industry as semiconductor light-emitting devices is limited, while the 1.4 μm band A (refer to FIG. 9) employed in one photoelectric switch according to the present invention is typically implementable by a semiconductor light-emitting device formed by a semiconductor mixed crystal of $In_{1-x}Ga_xAs_yP_{1-y}$ as hereinabove described.

As to a wavelength of 1.60 to 1.70 μm in the 1.6 to 1.7 μm band B employed in another photoelectric switch according to the present invention, this can typically be implemented by $In_{1-x}Ga_xAs_yP_{1-y}$. A wavelength of 1.60 to 1.80 μm is implementable by a semiconductor element formed by a semiconductor mixed crystal of an AlGaInSb system or an InPAsSb system.

On the other hand, it is also possible to implement a semiconductor light-emitting device used for the present invention by utilizing an effect of a super lattice in a semiconductor mixed crystal. While a crystal growth method is an important factor in fabrication of a semiconductor mixed crystal, a vapor phase growth method capable of further thin film formation, such as an MOVCD (Metal Organic Chemical Vapor Deposition) method, or a molecular beam epitaxy method, i.e., an MBE (Molecular Beam Epitaxy) method or the like is utilizable in addition to a traditional liquid phase growth (Liquid Phase Epitaxy) method. When such a technique is employed, it is possible to enlarge and control the range of an energy gap emittable by a general bulk semiconductor, and it is also possible to highly provide a degree of freedom also in controllability of the wavelength.

<1.2 Embodiments of Photoelectric Switches Utilizing Light of Specific Wavelengths>

Embodiments of the present invention which have been structured in accordance with the aforementioned principle are now described.

<1.2.1 First Embodiment>

Figure 10:
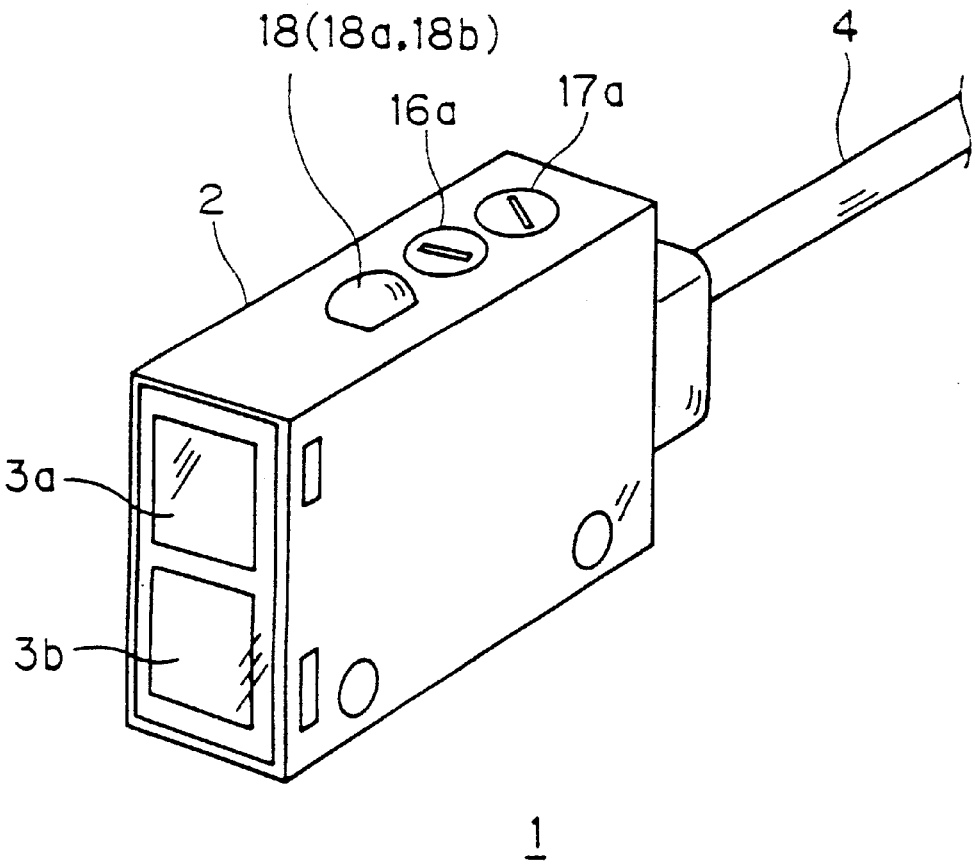
FIG. 10 is an appearance diagram of a reflection type photoelectric switch which is a preferred embodiment of the present invention utilizing light of a specific wavelength.
Figure 11:
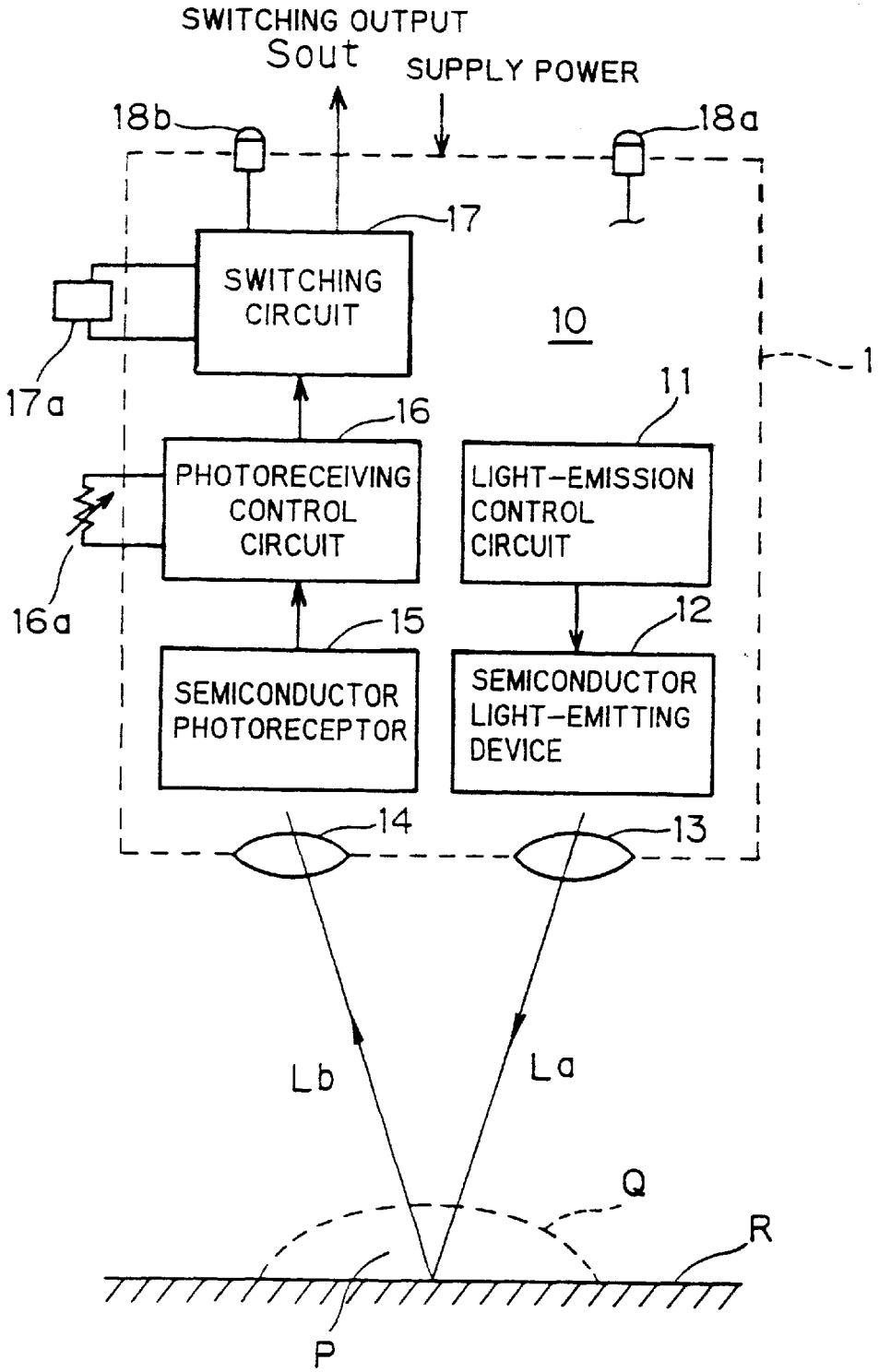
FIG. 11 is a diagram showing the internal structure and a use mode example of the photoelectric switch in FIG. 10.

FIG. 10 is an appearance diagram of a reflection type photoelectric switch 1 which is a first embodiment of the present invention, and FIG. 11 is a block diagram showing its internal structure. This photoelectric switch 1 is used as (1) a detection photoelectric switch for a substance containing an OH group (concretely a liquid mainly composed of water), or (2) a detection photoelectric switch for a substance containing a $CH_2$ group or a $CH_3$ group (concretely an organic liquid containing these groups) in accordance with an emission wavelength of a semiconductor light-emitting device contained therein (which will be described later).

As shown in FIGS. 10 and 11, the photoelectric switch 1 contains an element group 10 in the interior of a rectangular parallelopiped casing 2. This element group 10 is roughly classified into a projecting system, a photoreceiving system and a switching system. Excitation power is generated in a light emission control circuit 11 and supplied to a semiconductor light-emitting device 12 in the projecting system. This semiconductor light-emitting device 12 (i.e., a semiconductor light source), is selected to emit light of a wavelength selected from (1) the 1.4 μm band (1.40 to 1.50 μm) in case of a detection photoelectric switch for a substance containing an OH group, or (2) the 1.6 to 1.7 μm band (1.60 to 1.80 μm) in case of a detection photoelectric switch for a substance containing a $CH_2$ group or a $CH_3$ group, such as a semiconductor laser of an InGaAsP system, an AlGaInSb system or an InPAsSb system is used. Examples of wavelengths preferable in these ranges are 1.45 μm and 1.66 to 1.73 μm respectively.

Light La generated in the semiconductor light-emitting device 12 of FIG. 11 is projected from a transparent window 3a of FIG. 10 toward a prescribed detecting position P (FIG. 11) through a lens 13. A surface R on which this detecting position P is set is formed by a light reflecting material substantially not absorbing the light generated in the semiconductor light-emitting device 12. Therefore, the light La reaches the surface R and substantially its total quantity is reflected by this surface R when a detection object Q (a liquid mainly composed of water or an organic liquid) is not present on the detecting position P, and light La becomes reflected light Lb which returns to the photoelectric switch 1. On the other hand, most part of the light La is absorbed by the detection object Q when the detection object Q is present on the detecting position P, and the reflected light Lb becomes substantially zero or a relatively low light quantity.

The photoreceiving system of the photoelectric switch 1 comprises a semiconductor photoreceptor 15 and a photoreceiving control circuit 16. The light Lb incident from a transparent window 3b of FIG. 10 through a lens 14 of FIG. 11 is detected by this semiconductor photoreceptor 15. This photoreceptor 15 is formed by a photodiode, for example, and photoelectrically converts the received light. Its photoelectric conversion output is converted to a prescribed voltage or current in the photoreceiving control circuit 16. Concretely, this photoreceiving control circuit 16 discriminates a signal outputted from the semiconductor photoreceptor 15 in response to the level of the reflected light Lb by a prescribed threshold value, and converts the same to a binary signal indicating "photoreceiving state" and "non-photoreceiving state". Further, a gain control knob 16a accompanies this photoreceiving control circuit 16, and adjustment of detection sensitivity is possible by controlling the aforementioned threshold value in response to manipulation of this gain control knob 16a.

Further, the switching system of the photoelectric switch 1 comprises a switching circuit 17, and a detection pilot lamp 18b connected to this switching circuit 17. This switching circuit 17 is adapted to supply an ON/OFF switching output Sout to an apparatus (e.g., a controller for process control) in the exterior of the photoelectric switch 1 in response to a light detection result. Further, a switching direction changeover knob 17a accompanies the switching circuit 17, and it is possible to switch whether lighting of the detection pilot lamp 18b and "ON" of the switching output Sout are performed in photoreceiving or in non-photoreceiving by manipulating this switching direction changeover knob 17a. As shown in FIG. 10, the respective control knobs 16a and 17a are arranged on an upper surface of the casing 2, while the detection pilot lamp 18b is stored in a transparent pilot lamp hood 18 in a parallel manner with a power supply pilot lamp 18a.

As to the detection pilot lamp 18b and the power supply pilot lamp 18a, luminescent colors of these are different from each other, whereby it is possible to readily identify which is lighted. A supply power line of this photoelectric switch 1 and an extract line for the switching output Sout are connected to an external apparatus through a cable 4 of FIG. 10.

In the photoelectric switch of such a structure, the light absorption quantity varies with whether or not the detection object Q (a substance containing an OH group or a substance containing a $CH_2$ group or a $CH_3$ group) is present. Therefore, a signal level responsive to a quantity reaching the semiconductor photoreceptor 15 is discriminated with the threshold value, thereby automatically switching the switching output Sout in the light from the semiconductor light-emitting device 12, while lighting/extinguishment of the detection pilot lamp 18b is performed. Since the emission wavelength of the semiconductor light-emitting device is sharp, mixing of light of an extra wavelength is small, and detection accuracy is high. Further, this embodiment does not require a filter or the like such as that in case of employing a white light source, and the lenses 13 and 14 may be small ones, whereby of same is miniature as a whole, and its generality is high, too.

<1.2.2 Second Embodiment>

Figure 12:
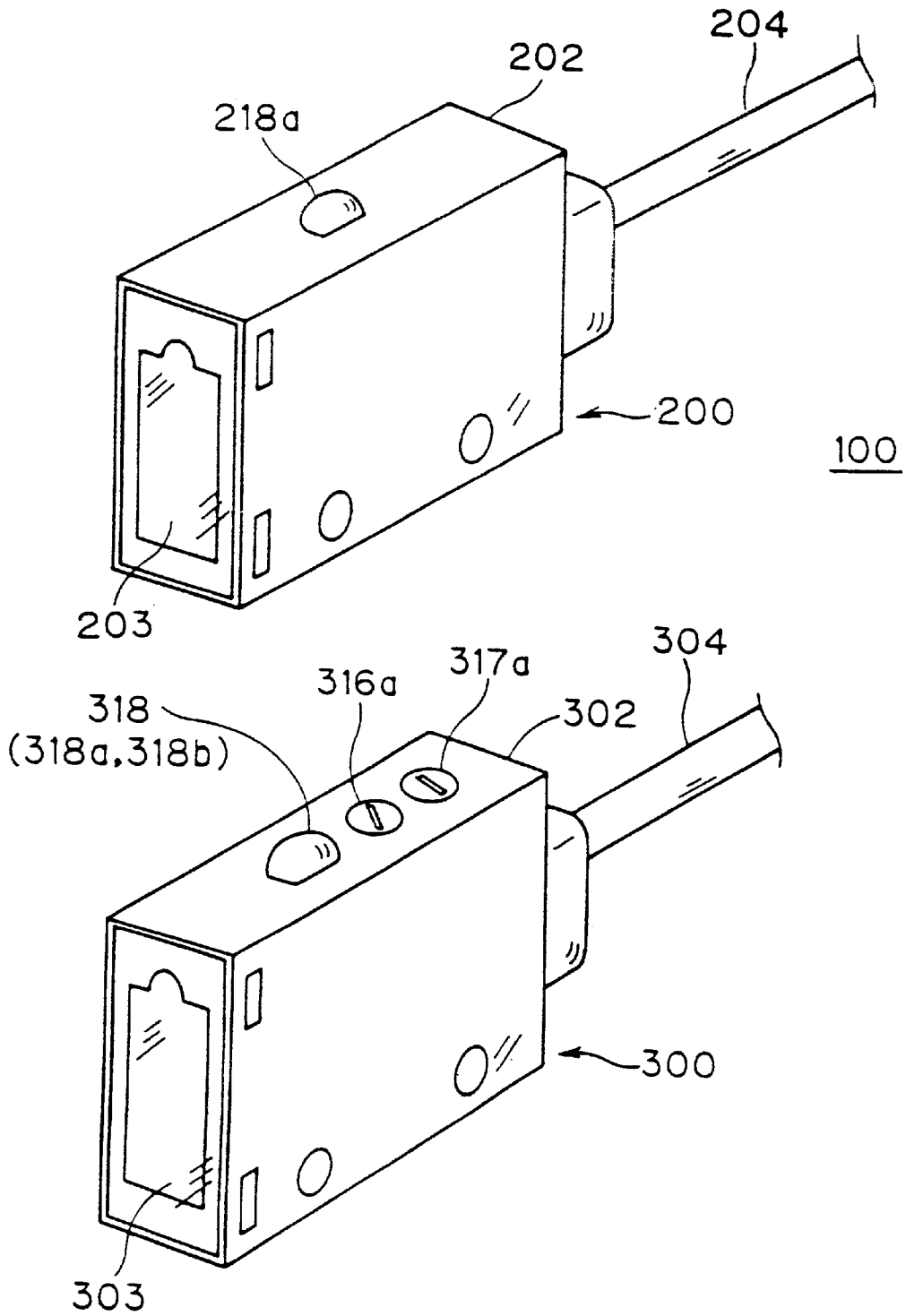
FIG. 12 is an appearance diagram of a transmission type photoelectric switch which is a preferred embodiment of the present invention utilizing light of a specific wavelength.
Figure 13:
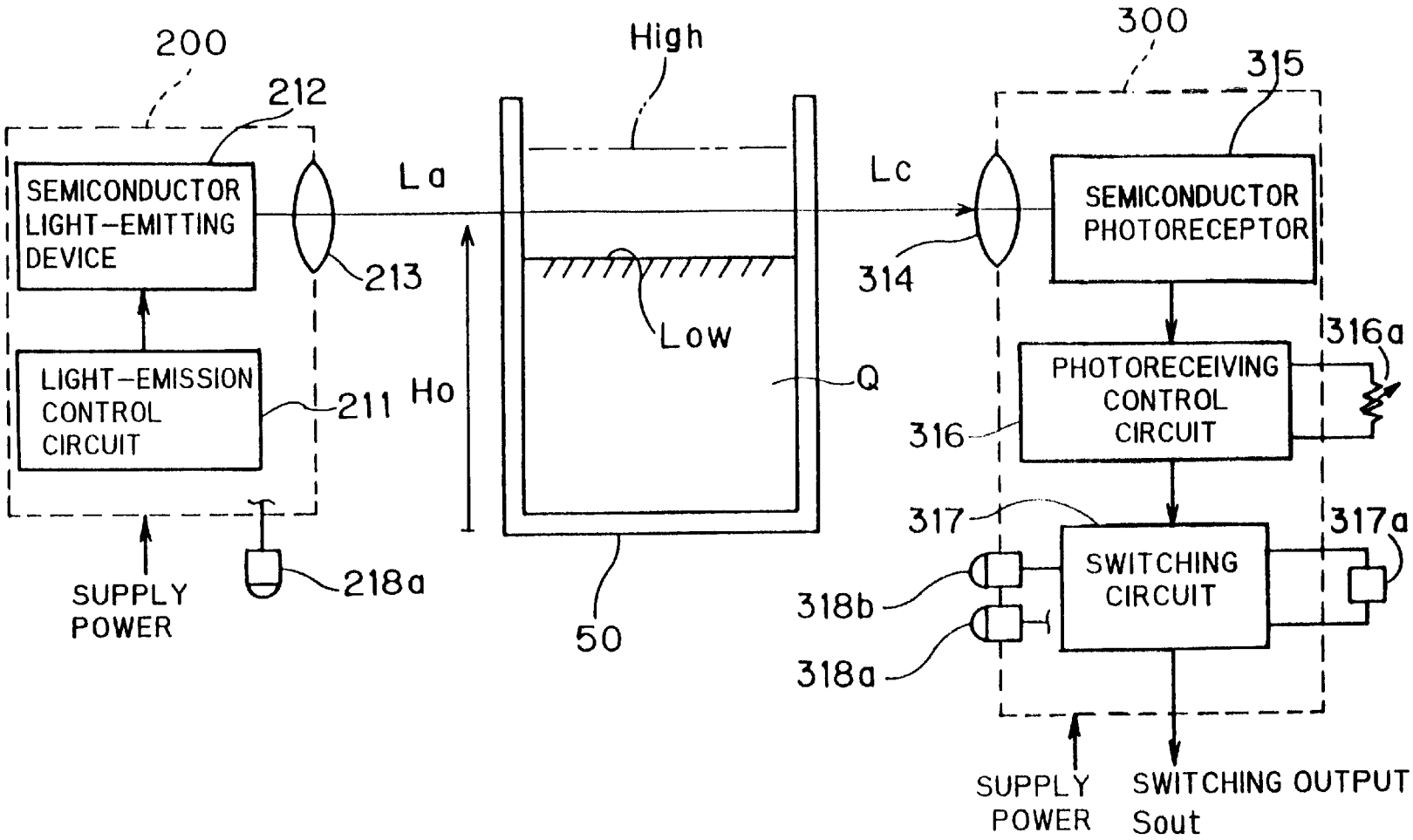
FIG. 13 is a diagram showing the internal structure and a use mode example of the photoelectric switch in FIG. 12.

FIG. 12 is an appearance diagram of a transmission type photoelectric switch 100 which is a second embodiment of the present invention, and FIG. 13 is a block diagram showing its internal structure. Among these, FIG. 13 illustrates a mode in which the photoelectric switch 100 is used for level detection of a liquid mainly composed of water or an organic liquid.

As shown in FIG. 12, this photoelectric switch 100 consists of a combination of a projecting part 200 and a photoreceiving part 300, and these are set on positions opposed to each other and used as shown in FIG. 13. In a space therebetween, a detection object Q is stored in a container 50 formed by a material having small light absorption in an emission wavelength of a semiconductor light-emitting device 212, such as glass, for example.

The projecting part 200 comprises a light emission control circuit 211 and the semiconductor light-emitting device 212 of FIG. 13 in the interior of a rectangular parallelopiped casing 202 of FIG. 12. A concrete structural example of this semiconductor light-emitting device 212 and its emission characteristics are similar to the first embodiment, and a semiconductor light-emitting device emitting light of a wavelength selected from (1) the 1.4 $\mu$m band (1.40 to 1.50 $\mu$m) in case of a detection photoelectric switch for a substance containing an OH group, or (2) the 1.6 to 1.7 $\mu$m band (1.60 to 1.80 $\mu$m) in case of a detection photoelectric switch for a substance containing a $CH_2$ group or a $CH_3$ group is used.

Light La generated in the semiconductor light-emitting device 212 is emitted from a transparent window 203 of FIG. 12 toward a prescribed set height HO of the container 50 through a lens 213. When the level of the detection object Q is at a height Low less than this set height H0, substantially of total quantity the light La reaches the photoreceiving part 300 as transmitted light Lc. When the level of the detection object Q is at a height High exceeding the set height H0, on the other hand, substantially the total quantity or most part of the light La is absorbed by the detection object Q, and the transmitted light Lc becomes substantially zero or a relatively low light quantity.

The photoreceiving part 300 comprises a semiconductor photoreceptor 315 and a photoreceiving control circuit 316 in a casing 302 of FIG. 12, and the semiconductor photoreceptor 315 among these is formed by a photodiode, for example. The light Lc incident through a transparent window 303 of FIG. 12 through a lens 314 of FIG. 13 is detected by this semiconductor photoreceptor 315, and its photoreceiving output is converted to a prescribed voltage or current in the photoreceiving control circuit 316. Its principle is similar to the photoreceiving control circuit 16 in the first embodiment. Further, a gain control knob 316a accompanies this photoreceiving control circuit 316 similarly to the first embodiment, whereby adjustment of detection sensitivity is possible.

The photoreceiving part 300 further comprises a switching circuit 317, and a detection pilot lamp 318b and a switching direction changeover knob 317a similar to the first embodiment accompanies this switching circuit 317.

It is also identical to the first embodiment that a power supply pilot lamp 318a in the photoreceiving part 300 is stored in a transparent pilot lamp hood 318 of FIG. 12 in a parallel manner with the detection pilot lamp 318b among power supply pilot lamps 218a and 318a in the projecting part 200 and the photoreceiving part 300. The projecting part 200 and the photoreceiving part 300 are connected to an external apparatus through cables 204 and 304 of FIG. 12 respectively.

The basic detection principle in this second embodiment is similar to the first embodiment and hence its repetitive description is omitted here, while the relation between the container 50 and the detection object Q of FIG. 13 is drinking water or an organic liquid stored in a transparent bottle, and in case of using this photoelectric switch 100 for control of its automatic filling, control such as stopping of filling can be performed by correctly detecting whether or not the liquid surface reaches the set height H0.

Incidentally, when the detection object Q has a certain degree of color, a certain degree of detection is possible in a conventional transmission type photoelectric switch, i.e., a photoelectric switch utilizing shading in the detection target Q. However, a large quantity of bubble foams are generated on the liquid surface in automatic filling of the liquid into the bottle, and it often happens that the bubble foams overflow toward the exterior of the bottle. Then, erroneous detection results since surfaces of the bubble foams shade or reflect the detection light.

On the other hand, this embodiment is based on a principle of light absorption, and the light absorption quantity increases in response to such a length that light passes through the liquid. In case of bubble foams, the interiors thereof are air, and hence absorption of light is small even if there are a number of bubble foams, and the bubble foams are not erroneously detected as the liquid surface. Thus, detection by absorption of light reflects only the level of the original liquid surface, and the detection becomes highly accurate.

<1.2.3 Modified Example of Photoelectric Switch Utilizing Light of Specific Wavelength>

In case of utilizing the photoelectric switch of the present invention for level detection of a liquid, it is possible to prepare the transmission type photoelectric switch 100 of the second embodiment in a plurality of sets, and set the same at different heights. Thus, the level of the liquid surface can be monitored at a plurality of heights. When the photoelectric switches 100 are arranged at the maximum level and the minimum level in consideration of filling errors in case of liquid filling into a bottle, for example, it is possible to identify only that having a liquid surface between the maximum level and the minimum level as an acceptable product.

Further, measuring light cannot be directly visually observed since the emission wavelength of the semiconductor light-emitting device is 1.4 to 1.5 $\mu$m or 1.6 to 1.8 $\mu$m, it is also possible to visualize the measuring light in a pseudo manner by separately providing an illumination light source generating visible light and making a visible spot from the illumination light source formed on the same position as a condensing position for the measuring light.

<2. Photoelectric Switches Utilizing Light of a Plurality of Different Wavelengths>

<2.1 Principle of Operation>

Before explaining concrete structures and operations of photoelectric switches utilizing light of a plurality of different wavelengths according to the present invention, an operation principle thereof is described while employing concrete examples. In the following, a photoelectric switch utilizing light of a plurality of different wavelengths is called a "multi-wavelength photoelectric switch".

<2.1.1 Example of Concrete Operation>

A multi-wavelength photoelectric switch described in the following example is adapted to detect, with respect to two types of detection, objects whose surface states (colors, gloss and the like) are different from each other, whether or not the detection objects contain certain specific substances even if light reflection levels vary with the difference of the surface states.

Figure 14A:
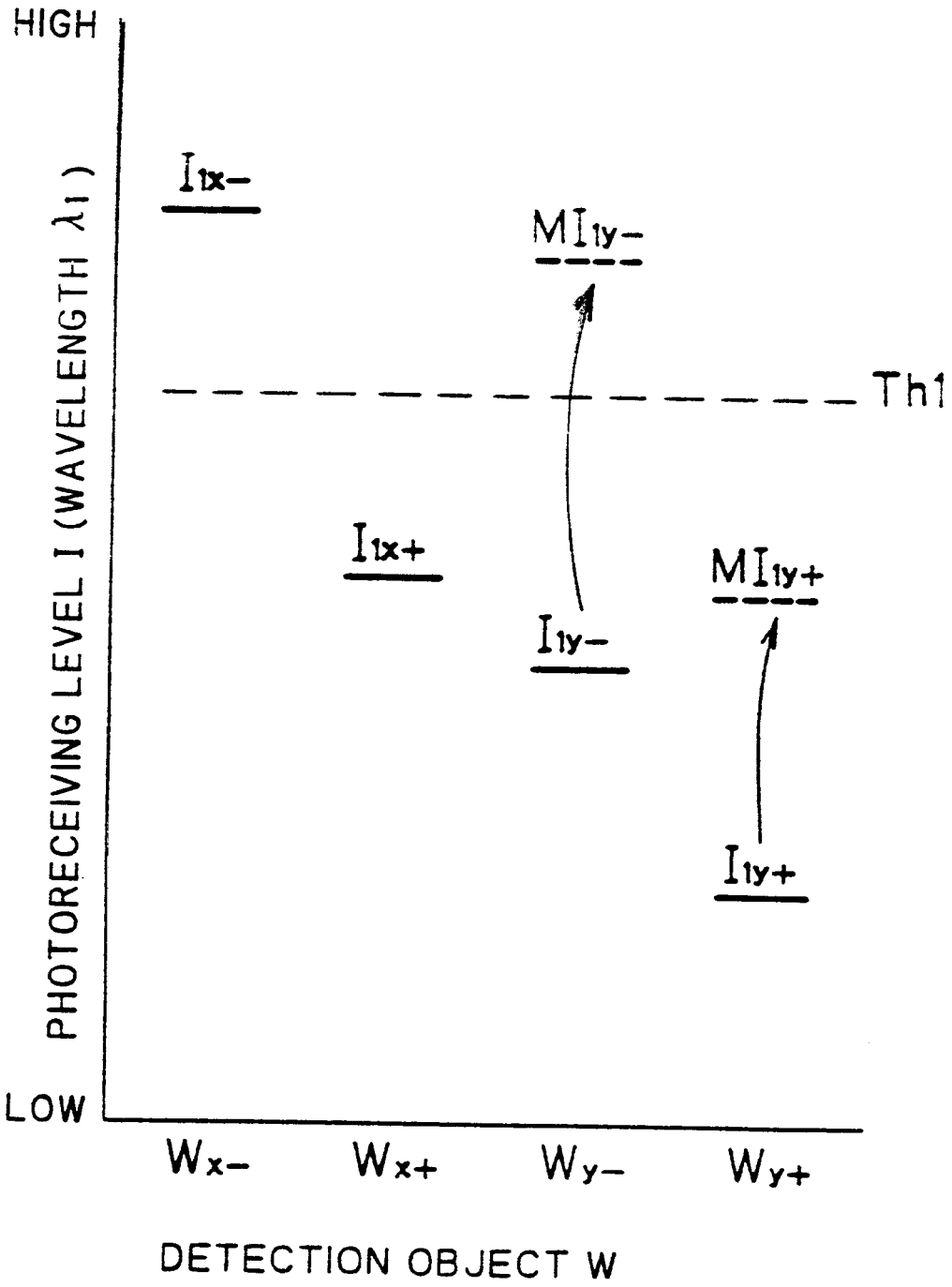
FIG. 14A and FIG. 14B are diagrams illustrating a method of detection in a preferred embodiment of the present invention utilizing light of a plurality of different wavelengths.
Figure 14B:
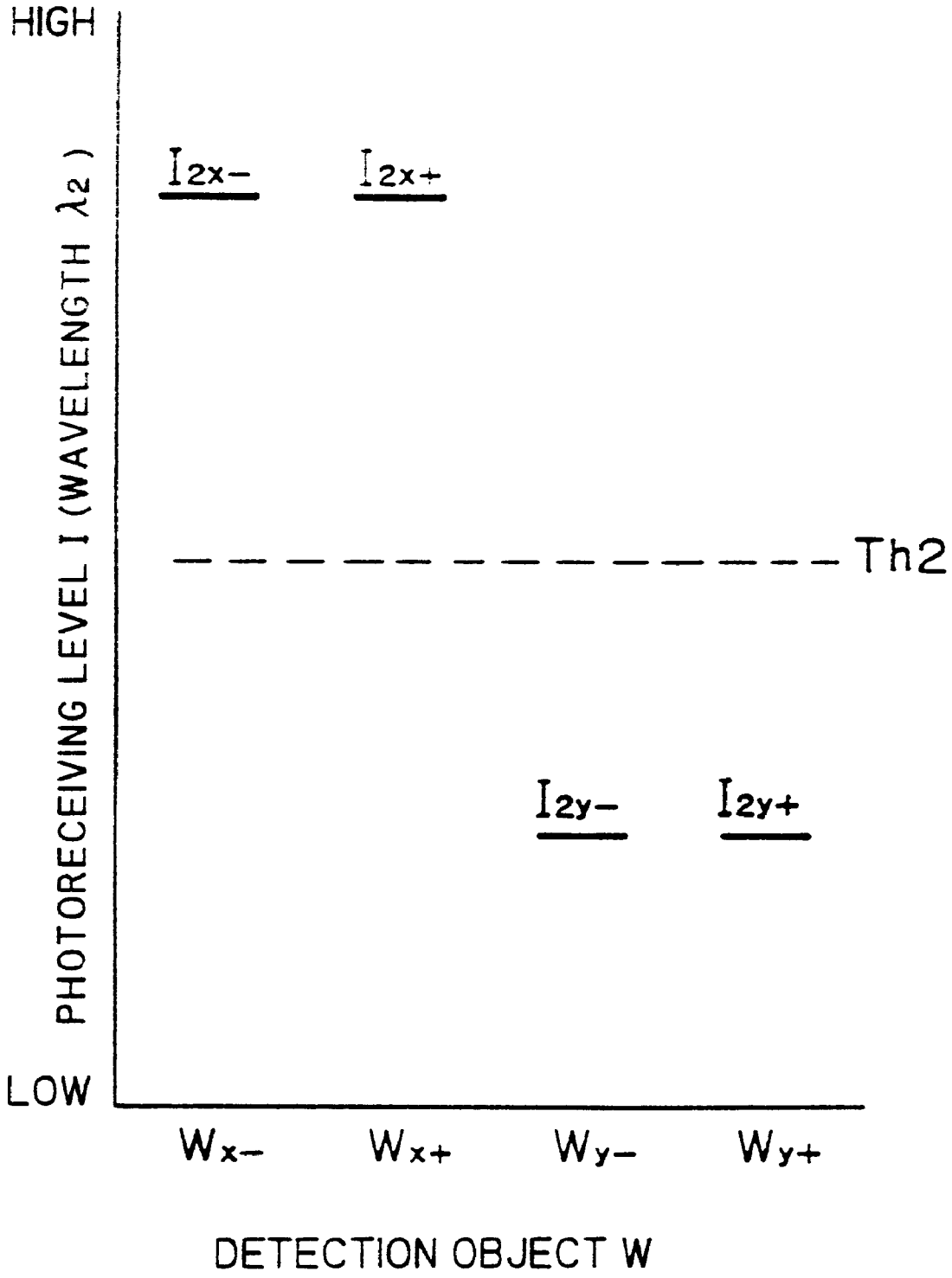

First, FIG. 14A and FIG. 14B are referred to. With respect to detection objects Wx and Wy (hereinafter these are referred to as "detection objects W" together) whose surface states are different from each other, those in states not containing a certain substance Z are assumed to be detection objects Wx− and Wy−, and those in states containing the substance Z are assumed to be detection objects Wx+ and Wy+.

For example,

Wx . . . white detection object,

Wy . . . black detection object,

Z . . . water,

Wx− . . . such a state that the white detection object contains no water,

Wy− . . . such a state that the black detection object contains no water,

Wx+ . . . such a state that the white detection object contains water, and

Wy+ . . . such a state that the black object contains water.

Further, it is assumed that there exist light of a first wavelength $\lambda$1 whose light reflection level is influenced by surface states of the detection objects W and is absorbed by the substance Z, and light of a second wavelength $\lambda$2 whose light reflection level is influenced by the surface states of the detection objects W but is not absorbed by the substance.

At this time, assuming that photoreceiving levels I of reflected light in case of irradiating the detection objects Wx−, Wx+, Wy− and Wy+ with the light of the first wavelength $\lambda$1 are I1x−, I1x+, I1y− and I1y+, and that photoreceiving levels I of reflected light in case of irradiating the detection objects Wx−, Wx+, Wy− and Wy+ with the light of the second wavelength $\lambda$2 of the same light quantity with the light of the first wavelength $\lambda$1 are I2x−, I2x+, I2y− and I2y+, these photoreceiving levels I become, as shown in FIGS. 14A and 14B:

I1x−>I1x+,

I1y−>I1y+,

I2x−=I2x+, and

I2y−=I2y+

However, this refers to such a case that the levels become I2x−>I2y− due to the surface states of the detection objects, namely, the detection object Wx− is larger in light reflectance than the detection object Wy− with respect to the wavelength $\lambda$2.

Here, when the levels become

I1x−>I1x+<I1y−>I1y+, as shown in FIG. 14A, it is not possible to detect whether or not the detection objects W contain the substance Z by only the light of the first wavelength $\lambda$1. Namely, it is not possible to set threshold values of the photoreceiving levels I detecting the difference between the photoreceiving levels I1x− and I1x+ and detecting the difference between the photoreceiving levels I1y− and I1y+.

Thus, a principle of first detecting the surface states of the detection objects W by the photoreceiving levels I of the reflected light by the light of the second wavelength $\lambda$2 and detecting whether or not the detection objects contain the substance Z on the basis of the results of this detection. Hereafter a method of detecting presence/absence of containment of the substance Z by employing the photoreceiving levels I of the reflected light of the light of the first and second wavelengths $\lambda$1 and $\lambda$2 is described in more detail.

The photoreceiving levels I of the reflected light by the light of the second wavelength $\lambda$2 are, as shown in FIG. 14B:

I2x−=I2x+ and

I2y−=I2y+, and,

I2x−>I2y−, and hence it is possible to detect whether a detection object W is a detection object Wx or a detection object Wy when identifying the photoreceiving level as to the light of the second wavelength $\lambda$2. Namely, when a threshold value Th2 satisfying I2x−>Th2<I2y−, and, I2x+<Th2<I2y+, is set, it is possible to detect that the object is the detection object Wx if the photoreceiving level I is higher th an the threshold value Th2, or the detection object Wy if lower than the threshold value Th2.

When being detected as the detection object Wy, it is possible to set a threshold value Th1 which becomes $$I1x- > Th1 < I1x+,$$

and, $$M \cdot I1y- > Th1 < M \cdot I1y+,$$

by multiplying the photoreceiving levels I1y− and I1y+ of the reflected light by an amplification factor M (constant). Namely, it comes to that it is possible to detect that the detection object does not contain the substance Z when the photoreceiving level I of the reflected light is higher than the threshold value Th1, and that the object contains the substance Z when lower than the threshold value Th1.

Thus, it becomes possible to properly detect surface states of the detection objects W and presence/absence of containment of the specific substance Z, which may have been impossible to detect in general.

<2.1.2 General Operation Principle and its Utilization Modes>

While the concrete operation principle of detecting whether or not the detection objects Wx and Wy of different surface states contain the substance Z by the light of two different wavelengths has been described, this is an operation principle of irradiating a detection object with light of a plurality of different wavelengths and correcting a received light-quantity of another wavelength from the detection object on the basis of a received light-quantity of one wavelength from the detection object. Thus, a plurality of types of detection from the detection object are performed.

As a concrete example utilizing such an operation principle, a method of utilizing visible light with respect to detection of colors while utilizing light whose wavelength is in the range of 1.40 to 1.50 μm for detection of presence/absence of water in case of detecting the colors of the detection objects and presence/absence of water which is a substance containing an OH group described in the example of the aforementioned operation principle can be listed, for example.

In case of detecting the colors of the detection objects and a material such as synthetic resin which is a substance containing a $CH_2$ group and/or a $CH_3$ group, on the other hand, a method of utilizing visible light for detection of the colors and utilizing light whose wavelength is in the range of 1.60 to 1.80 μm for detection of the material containing a $CH_2$ group or a $CH_3$ group can be listed.

<2.2 Embodiments of Photoelectric Switch Utilizing Light of a Plurality of Different Wavelengths>

<2.2.1 Third Embodiment>

Figure 15:
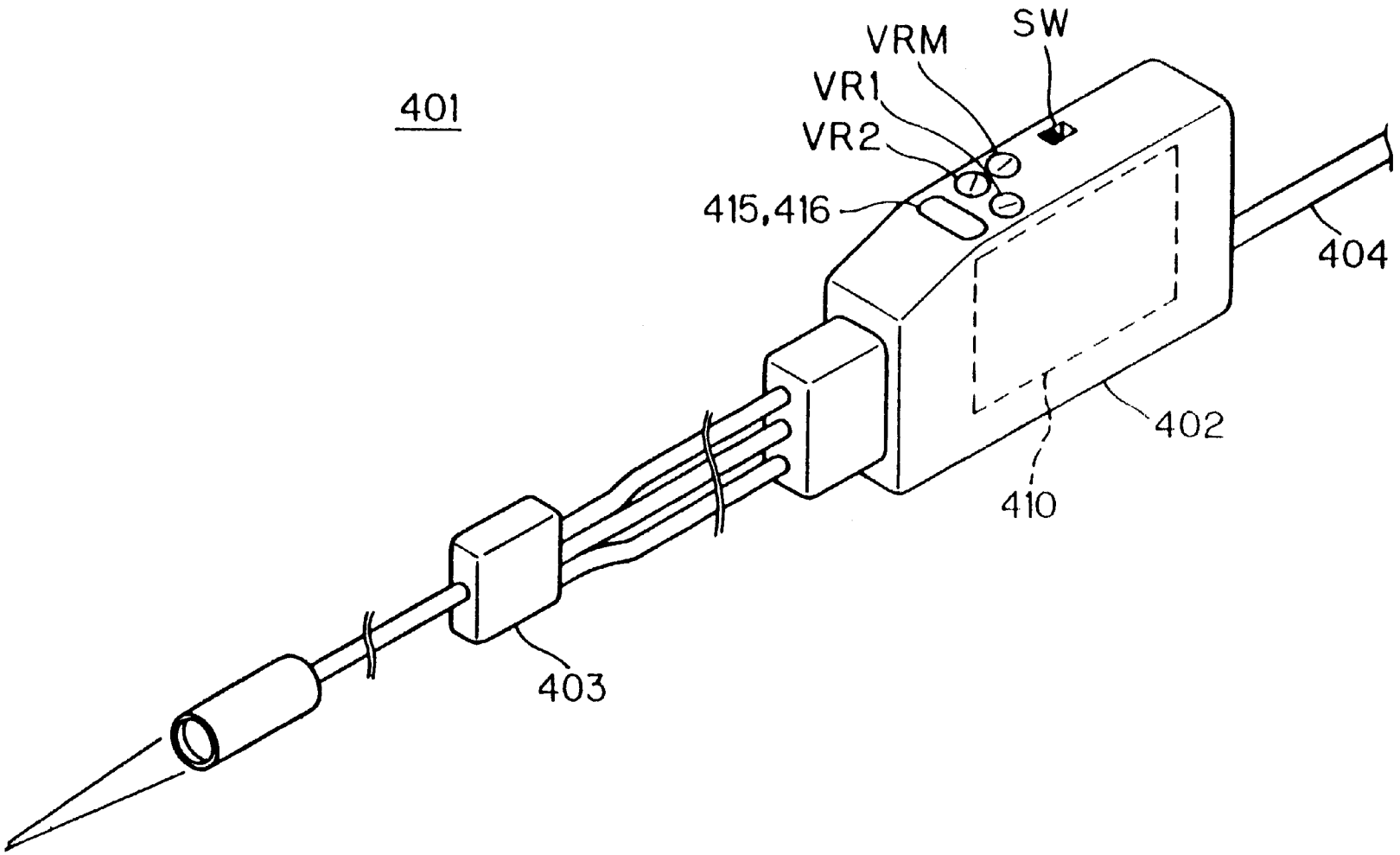
FIG. 15 is an appearance diagram of a photoelectric switch which is a preferred embodiment of the present invention utilizing light of a plurality of different wavelengths.
Figure 16:
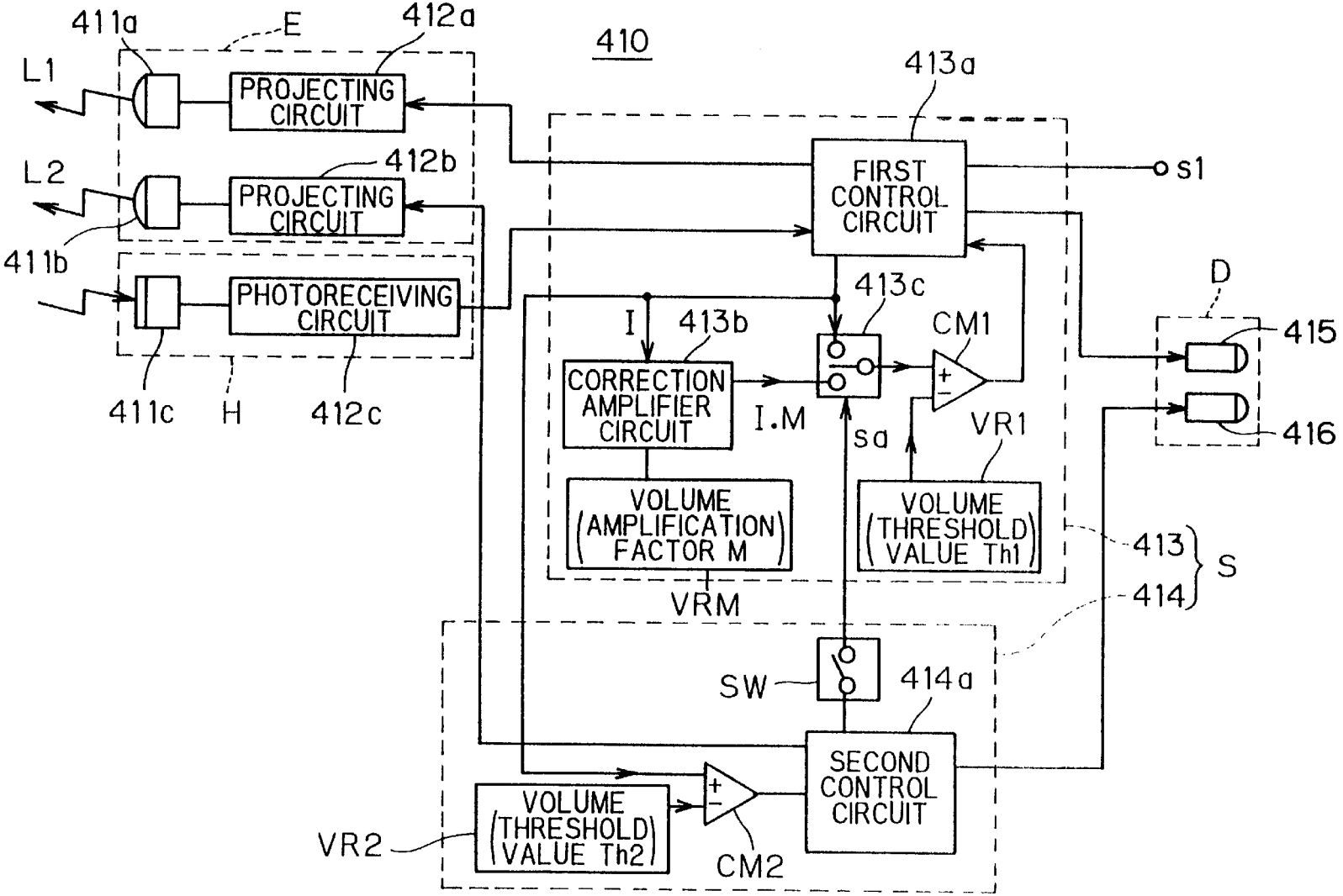
FIG. 16 is a diagram showing the internal structure of the photoelectric switch shown in FIG. 15.

FIG. 15 is an appearance diagram of a reflection type multi-wavelength photoelectric switch 401 which is an embodiment of the present invention, and FIG. 16 is a diagram showing the internal structure of the multi-wavelength photoelectric switch 401. The multi-wavelength photoelectric switch 401 is adapted to detect whether or not detection objects W (FIG. 19) contain water as a typical example of a substance having an OH group, without being influenced by surface states thereof with respect to two types of detection objects Wx and Wy whose surface states (colors, gloss and the like) are different from each other. The structure of the multi-wavelength photoelectric switch 401, an irradiation method of light, and a method of photoreceiving are now described.

The multi-wavelength photoelectric switch 401 is formed by a rectangular parallelopiped casing 402, a circuit group 410 in the interior of the casing 402, a fiber unit 403 which is an optical path means projecting light to the detection objects W while sending back reflected light from the detection objects W, and a cable 404 transmitting signals of detection results with respect to the detection objects to a prescribed control apparatus.

As shown in FIG. 16, the circuit group 410 is roughly classified into a projecting system E which is light emission means, a photoreceiving system H which is photoreceiving means, a processing system S which is switching means, and a display system D for performing operation display. The projecting system E is formed by a light-emitting device 411a generating invisible infrared light L1 belonging to the waveband of 1.40 to 1.50 μm, a light-emitting device 411b generating visible red light L2, a projecting circuit 412a and a projecting circuit 412b driving these light-emitting devices 411a and 411b on the basis of signals from the processing system S. The photoreceiving system H is formed by a photoreceptor 411c receiving reflected light from the detection objects, and a photoreceiving circuit 412c driving the photoreceptor 411c while processing a photoreceiving signal, and transmitting the photoreceiving signals to the processing system S. The processing system S is formed by a signal processing circuit 413 supplying a projection timing signal to the projecting circuit 412a while receiving the photoreceiving signal from the photoreceiving circuit 412. A sensitivity correction circuit 414 transmits a sensitivity correction signal to the projecting circuit 412b. The signal processing circuit 413 and the sensitivity correction circuit 414 transmit signals to the display system D, while the signal processing circuit 413 generates an output signal s1 as a switching signal. The display system D is formed by a first detection pilot lamp 415 and a second detection pilot lamp 416, and displays operating states of the signal processing circuit 413 and the sensitivity correction circuit 414.

The signal processing circuit 413 is provided with a first control circuit 413a controlling the whole signal processing circuit 413. A photoreceiving level I of the photoreceiving signal is supplied to a comparator CM1 through a switch 413c which is switched by receiving a signal sa from the sensitivity correction circuit 414. A threshold value Th1 which is set in a volume VR1 is also supplied to this comparator CM1, so that the photoreceiving level I is compared with the threshold value Th1 and this comparison result is transmitted to the first control circuit 413a.

Further, the photoreceiving level I of the photoreceiving signal is also supplied to a correction amplifier circuit 413b. A volume VRM is connected to this correction amplifier circuit 413b, so that its amplification factor M can be adjusted by adjustment of the volume VRM. When the switch 413c is switched toward this correction amplifier circuit 413b side, a photoreceiving level I·M after correction by amplification is compared with the threshold value Th1 in the comparator CM1.

On the other hand, the sensitivity correction circuit 414 is provided with a second control circuit 414a controlling the whole sensitivity correction processing circuit 414. Further, there exists a volume VR2 adjusting another threshold value Th2, and the photoreceiving signal I is compared with this threshold value Th2 in a comparator CM2, so that its comparison result is outputted as the signal sa.

A sensitivity correction circuit changeover switch SW employed in case of adjusting a sensitivity correction quantity is provided on a transmission path of the signal sa. The volumes VRM, VR1 and VR2 and the sensitivity correction circuit changeover switch SW are arranged on the casing 402 as shown in FIG. 15, so that the same can be adjusted from the exterior.

Figure 17:
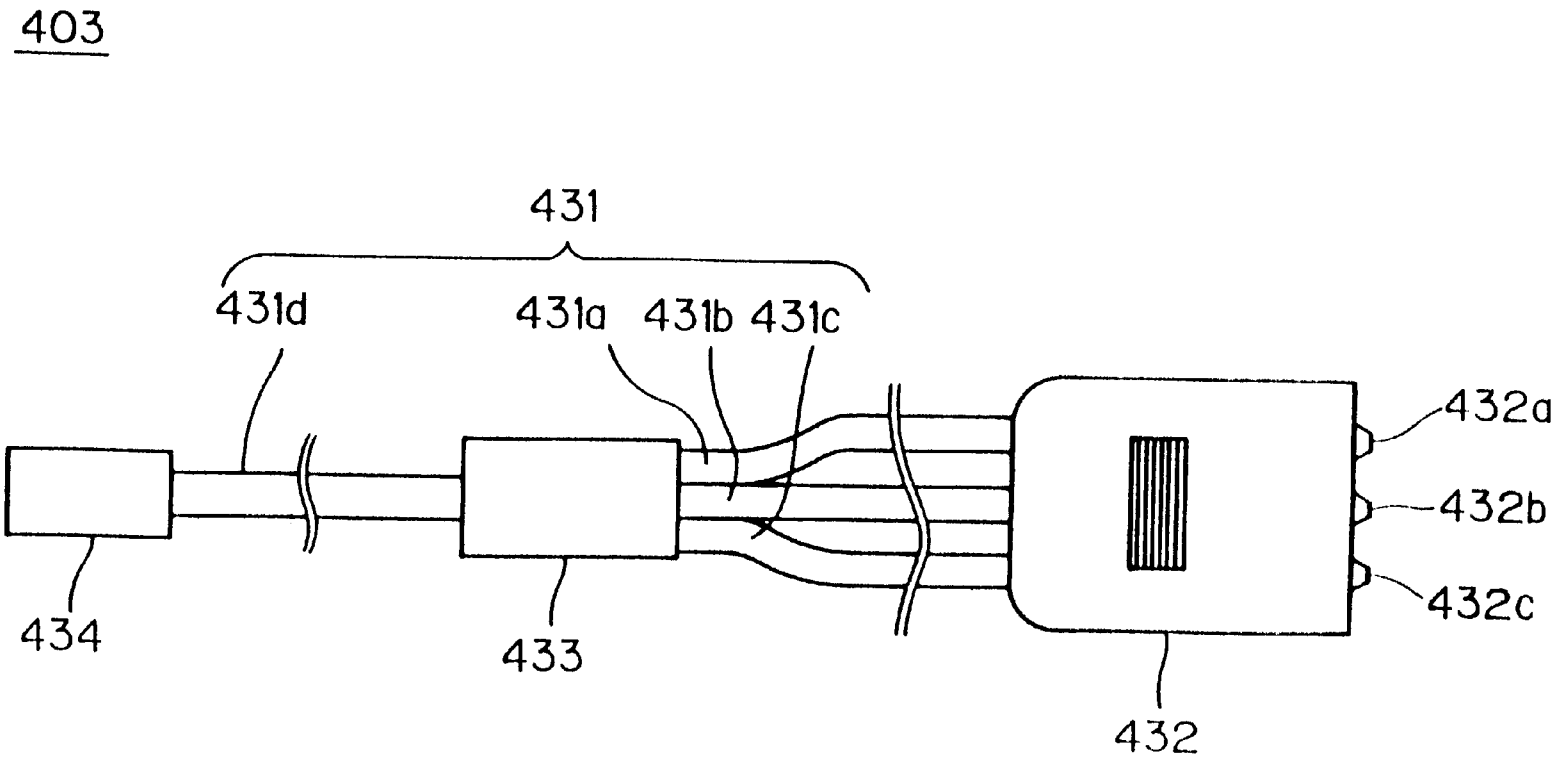
FIG. 17 is a diagram showing a fiber unit of the photoelectric switch shown in FIG. 15.
Figure 18:
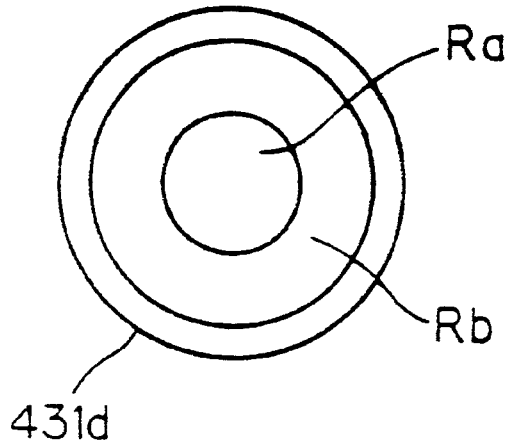
FIG. 18 is a diagram showing one section of a fiber part shown in FIG. 17.

As shown in FIG. 17, the fiber unit 403 is formed by a fiber part 431 transmitting light, a connector 432 connected to the casing 402, a superposition part 433 guiding light transmitted in the fiber on the same optical path, and a forward end portion 434. The fiber part 431 is formed by three fibers 431a, 431b and 431c connected to the connector 432 and the superposition part 433, and a fiber 431d connected to the superposition part 433 and the forward end portion 434. Fiber 431d is in a concentric double structure whose section is divided into an inner region Ra and an outer region Rb as shown in FIG. 18. Connection ports 432a, 432b and 432c are provided on the connector 432, and connected to the fibers 431a, 431b and 431c respectively in the interior of the connector 432. When the connector 432 is connected to the casing 402, light from the light-emitting devices 411a and 411b is incident upon the connection ports 432a and 432b, and the light is superposed in the superposition part 433, and transmitted through the inner region Ra of the fiber 431d, to outgo on the same optical path through a lens provided on the forward end portion 434. Conversley, reflected light from the detection objects is incident from the forward end portion 434 and transmitted through the outer region Rb of the fiber 431d, to be guided to the photoreceptor 411c from the fiber 431c through the connection port 432c.

As an example illustrating the operation of the multi-wavelength photoelectric switch 401 shown in FIG. 15, description is now made on an applied example of employing a white piece Wx of paper and a black piece Wy of paper as the detection objects W having different surface states and detecting whether or not water is contained in the pieces of paper, i.e., whether the pieces of paper are wet or dry as detection of containment of the substance Z having an OH group in a processing step for the pieces of paper. In correspondence to the symbols employed in the explanation of the already described operation principle, a dry white piece of paper is denoted by Wx−, a wet white piece of paper is denoted by Wx+, a dry black piece of paper is denoted by Wy−, and a wet black piece of paper is denoted by Wy+, and photoreceiving levels I for reflected light obtained when these are irradiated with a first wavelength λ1 corresponding to the wavelength of the infrared light L1 and a second wavelength λ2 corresponding to the wavelength of the red light L2 are denoted by I1x−, I1x+, I1y− and I1y+, and I2x−, I2x+, I2y− and I2y+ respectively.

Figure 19:
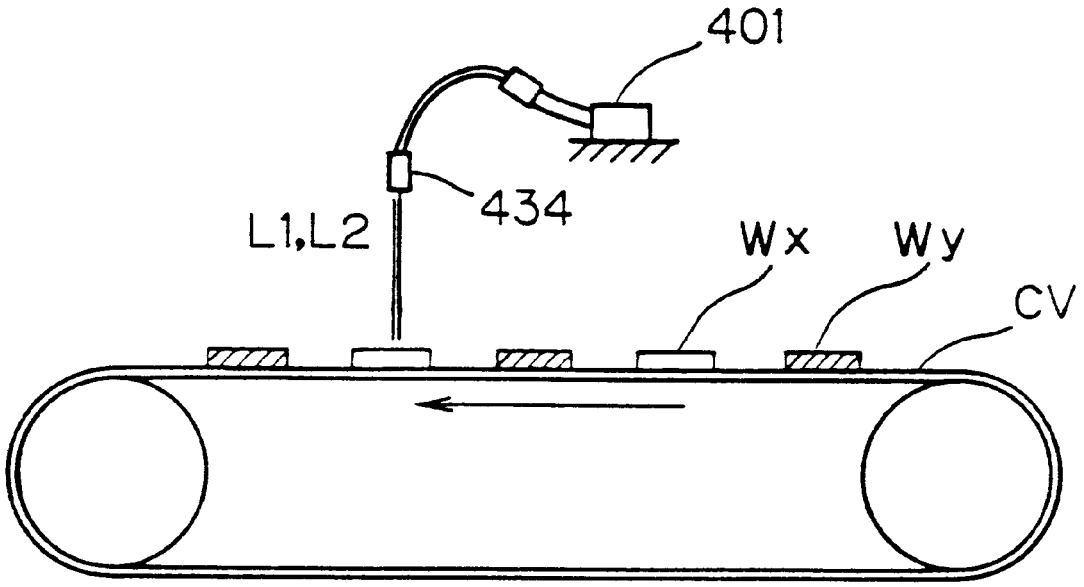
FIG. 19 is a diagram showing one application example of the photoelectric switch shown in FIG. 15.

FIG. 19 is a diagram showing this applied example of the multi-wavelength photoelectric switch 401 in this embodiment. In the figure, a conveyor CV simultaneously carries the white piece Wx of paper and the black piece Wy of paper in the direction of arrow. First, a method of setting the threshold value Th1, the threshold value Th2 and the amplification factor M employed by the multi-wavelength photoelectric switch 401 described with reference to the method of detection are described.

(1) In a state that the sensitivity correction circuit changeover switch SW is OFF, the volume VR1 is so adjusted that the first detection pilot lamp 415 is lighted with respect to the dry white piece Wx− of paper and extinguished with respect to the wet white piece Wx+ of paper. With respect to the infrared light L1 of the first wavelength λ1 emitted from the multi-wavelength photoelectric switch 401, the threshold value Th1 is adjusted to satisfy:

$$I1x- > Th1 < I1x+$$

with respect to the photoreceiving level I1x− and the photoreceiving level I1x+, due to this operation.

(2) In a state that the sensitivity correction circuit changeover switch SW is ON, the volume VR2 is so adjusted that the second detection pilot lamp 416 is lighted with respect to the white piece Wx of paper (may be either wet or dry) and extinguished with respect to the black piece Wy of paper (may be either wet or dry). With respect to the red light L2 of the second wavelength λ2 emitted from the multi-wavelength photoelectric switch 401, the threshold value Th2 is adjusted to satisfy:

$$I2x- > Th2 < I2y-, \text{ (where } I2x+=I2x- \text{ and } I2y+=I2y-)$$

with respect to the photoreceiving level I2x− (or I2x+) and the photoreceiving level I2y− (or I2y+), due this operation.

(3) Remaining in the state that the sensitivity correction circuit changeover switch SW is ON, the volume VRM is so adjusted that the first detection pilot lamp 415 is lighted with respect to the dry white piece Wx− of paper and the dry black piece Wy− of paper, and extinguished with respect to the wet white piece Wx+ of paper and the wet black piece Wy+ of paper. Due to this operation, the amplification factor M is adjusted to satisfy:

$$M \cdot I1y- > Th1 < M \cdot I1y+$$

Due to the aforementioned adjustment, the multi-wavelength photoelectric switch 401 is adjusted to satisfy the conditions described with reference to the description of the principle of detection (FIG. 14A and FIG. 14B). Namely, whether or not the pieces of paper are "black" or "white" becomes determinable by comparison of the photoreceiving levels as to the light L2 of the second wavelength λ2 and the threshold value Th2, and whether or not the pieces of paper are wet becomes determinable by comparison of the photoreceiving levels as to the light L1 of the first wavelength λ1 themselves or results obtained by amplifying/correcting the same with the amplification factor M, and the threshold value Th1.

Figure 20:
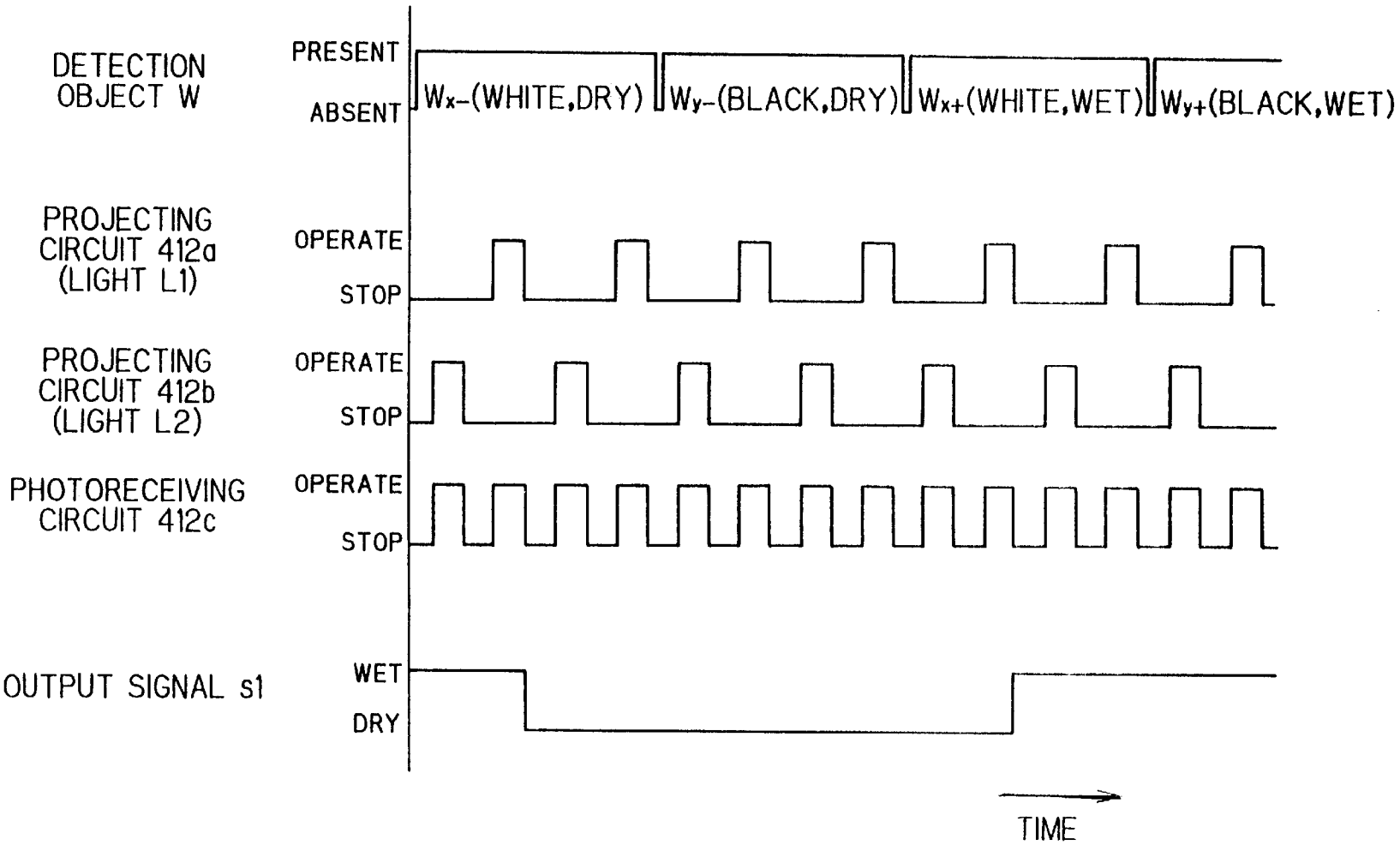
FIG. 20 is a timing chart in one application example of the photoelectric switch shown in FIG. 15.

FIG. 20 is a timing chart in this applied example. The infrared light L1 of the first wavelength λ1 and the red light L2 of the second wavelength λ2 are alternately projected by a control signal from the signal processing circuit 413, and the photoreceiving circuit 412c is driven when either is projected to obtain the photoreceiving signal I.

This photoreceiving signal I is compared with the threshold value Th2 in the comparator CM2, and the determination signal sa of "black or white" is obtained in response to the comparison result. This signal sa is supplied to the switch 413c, and the switch 413c is switched toward the correction amplifier circuit 413b by this signal sa in case of "black". Therefore, the photoreceiving I is inputted in the comparator CM1 after amplified/corrected with the amplification factor M to become the corrected photoreceiving level I·M. Thus, "whether wet or not" is determined, and the determination result is transmitted to the first control circuit 413a.

If the comparison result in the comparator CM2 is "white", on the other hand, the switch 413c is switched toward the first control circuit 413a by the signal sa, and the photoreceiving signal I is directly inputted in the comparator CM1 and compared with the threshold value Th1. Thus, "whether wet or not" is determined, and the determination result is transmitted to the first control circuit 413a.

The first control circuit 413a obtains the determination result of "whether wet or not" regardless of whether the piece of paper is "white" or "black", and outputs the result as a switching output signal s1 to the exterior.

When information also including the color of the piece of paper is to be obtained as the switching output signal s1, the signal sa may be outputted also to the first control circuit 413a, so that this first control circuit 413a identifies and outputs four states combining these two types of information, i.e., "whether white or black" and "whether wet or not" with four values of 2-bit digital signals.

Thus, switching signals which are determination results of "whether wet or not" as to the four types of detection objects Wx− to Wy+ can be correctly obtained regardless of the colors thereof, as shown in FIG. 20.

Although not shown in FIG. 20, the output signal s1 is outputted after light is received in the photoreceptor 411c several times in practice, in order to stabilize the results of detection.

In the multi-wavelength photoelectric switch 401 in this embodiment, it is possible to detect whether wet or not with respect to the pieces of paper which are the two types of detection objects Wx and Wy whose surface states are different to white and black by employing the light of the two different wavelengths λ1 and λ2 and making correction by the correction amplifier circuit 413b and the like.

Further, the light of the two different wavelengths λ1 and λ2 are guided onto the same optical path through the fiber unit 403, whereby there is no need to set two photoelectric switches dissimilarly to the prior art, the equipment design is simplified, and correct detection can be performed.

In case of using the photoelectric switch for the use shown in FIG. 19, also conceivable is a technique (hereinafter "comparative technique") of providing a first photoelectric switch detecting only presence/absence of a detection object on an upstream side of a flow of the detection object and a second photoelectric switch provided on a downstream side for performing a determination on the state of the detection object only when the aforementioned first photoelectric switch detects the detection object. However, not only a plurality of photoelectric switches are required in such a case but the optical path of the first photoelectric switch and the optical path of the second photoelectric switch separate from each other, and hence detection in the second photoelectric switch must be performed in a delay by a prescribed time from a point of time when the first photoelectric switch detects presence/absence of the detection object.

Therefore, not only such delay control is necessary, but there may be such a case that the detection becomes incorrect. When the time when the detection object moves from the position of the first photoelectric switch to the position of the second photoelectric switch fluctuates by temporal fluctuation of the carriage speed, for example, a detection error inevitably occurs in the structure of operating the second photoelectric switch after the aforementioned constant delay time.

On the other hand, two types of detection are performed on the same optical path in the aforementioned embodiment of the present invention, whereby delay processing of timing becomes unnecessary, and no detection error following the delay takes place.

Further, the light of the wavelength of 1.40 to 1.50 μm is employed as the light of the first wavelength λ1, whereby presence/absence of containment of water which is the substance having an OH group can be detected.

In addition, one of the projected light is the red light which is visible light, whereby the projecting position can be readily recognized even if the other wave is invisible light.

<2.2.2 Fourth Embodiment>

While the third embodiment performs correction by employing the light of the second wavelength λ2, the light of the first wavelength λ1 and the light of the second wavelength may be employed as completely independent uses, as a matter of course. Also in this case, installation of a photoelectric switch is simplified, and delay processing of operation timing becomes unnecessary.

Figure 21:
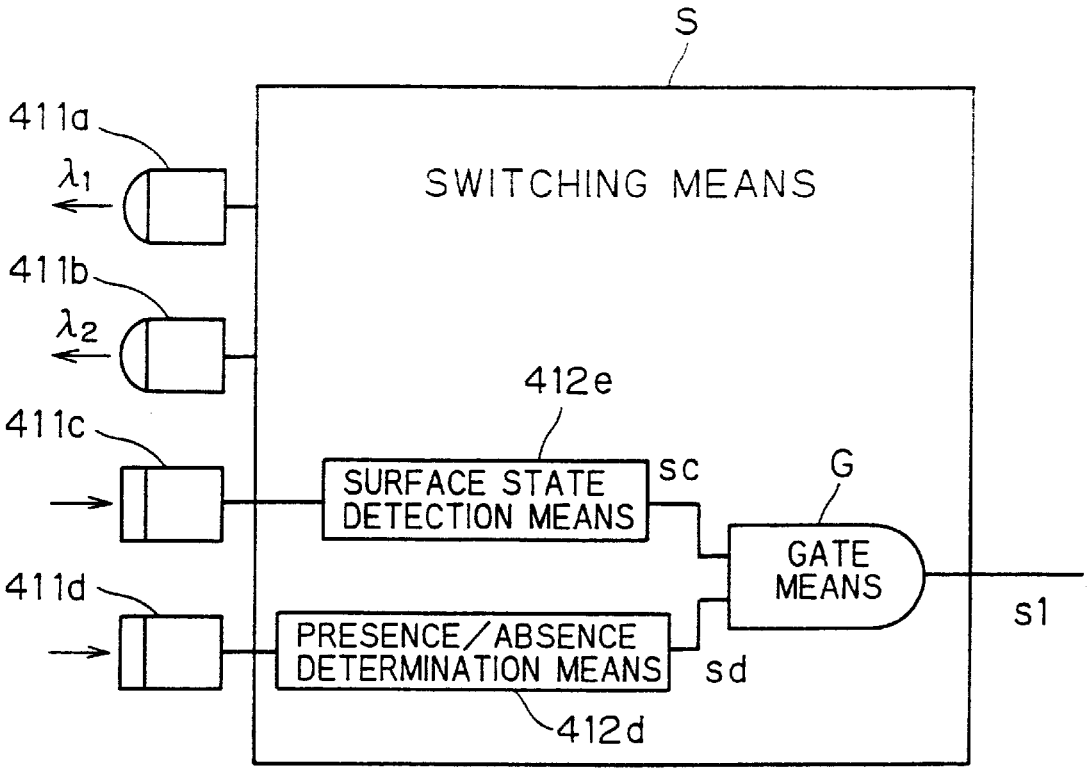
FIG. 21 is a diagram showing a part of an internal structure in a photoelectric switch which is a preferred embodiment of the present invention separately utilizing light of a plurality of different wavelengths.

FIG. 21 is a diagram showing an example of a photoelectric switch employing light of one wavelength for detection of a surface state of a detection object and light of another wavelength for detection of presence/absence of the detection object. This photoelectric switch is in a structure substantially similar to the photoelectric switch of the third embodiment, but different in that it contains two photoreceptors 411c and 411d and surface state detection means 412e connected to these photoreceptors 411c and 411d, presence/absence detection means 412d, and gate means G.

As shown in FIG. 21, light of a first wavelength λ1 directed to detection of the surface state of the detection object is emitted from a light-emitting device 411a by a signal from switching means S, and reflected light from the detection object is received by the photoreceptor 411c. Further, light of a second wavelength λ2 directed to determination of presence/absence of the detection object is emitted from the light-emitting device 411b, and its reflected light is received by the photoreceptor 411d. A signal from the photoreceptor 411c is compared with a prescribed threshold value in the surface state detection means 412e and becomes a surface state signal sc, and a signal from the photoreceptor 411d is also compared with a prescribed threshold value in the presence/absence determination means 412d and becomes a presence/absence determination signal sd to be transmitted to the gate means G together. The surface state signal sc is gated by the gate means G operating by the presence/absence determination signal sd, and becomes an output signal s1. Therefore, the determination result of the surface state of the detection object can be obtained only when the detection object is present.

Consequently, it is not necessary to separately provide a photoelectric switch determining presence/absence of the detection object, and delay setting of operation timing is also unnecessary.

<2.2.3 Modification of Multi-Wavelength Photoelectric Switch>

While the description has been made on the embodiment of the multi-wavelength photoelectric switch according to the present invention, the present invention is not restricted to the aforementioned embodiment, but the following modifications are also possible.

Although the above embodiment employs the light of the wavelength of 1.40 to 1.50 μm as the light of the first wavelength, that employing light of a wavelength of 1.60 to 1.80 μm is also employable. In this case, detection becomes possible as to presence/absence of containment of a substance having a $CH_2$ group and/or a $CH_3$ group.

Although the aforementioned embodiment employs a liquid (water) as a certain substance to be detected, a solid may be employed as described with reference to FIG. 7 and FIG. 8. It can be utilized for detecting whether or not surface treatment is performed with respect to a detection object surface-treated with transparent resin, for example, with no influence by its color or the like.

While the aforementioned embodiment is a reflection type multi-wavelength photoelectric switch, the same can be employed as a transmission type multi-wavelength photoelectric switch by guiding light transmitted through a detection object to the photoreceptor by employing another fiber.

While the aforementioned embodiment employs light of two different wavelengths as light of a plurality of different wavelengths, light of at least three different wavelengths is also employable, as a matter of course.

While the aforementioned embodiment employs one photoreceptor as the photoreceptor, light from the detection object may be received by a plurality of photoreceptors by employing a prism or an optical filter. Further, light of at least two different wavelengths may be successively projected for selecting a photoreceiving signal from at least one photoreceptor while taking synchronization with a projecting circuit and separating the photoreceiving signal. In addition, it is also possible to separate a photoreceiving signal from one photoreceptor by employing an electric filter such as Fourier transformation, by rendering frequencies (pulse widths) of projection pulses of light of at least two different wavelengths.

While the threshold values Th1 and Th2 are adjusted by the volumes in the circuit illustrated in FIG. 16, the large-small relations between the photoreceiving levels and the threshold values are relative. Therefore, the threshold values Th1 and Th2 may be fixed at default values, and the photoreceiving levels I before the comparators CM1 and CM2 may be amplified respectively by the amplification factors adjusted previously for equivalently previously adjusting the relations with the threshold values Th1 and Th2. Similarly, the threshold values supplied to the comparator CM1 in response to the determination results of "black" and "white" may be switched between the threshold value "Th1" and a threshold value "Th1/M", in place of providing the correction amplifier circuit 413b for the photoreceiving levels I.

Figure 22A:
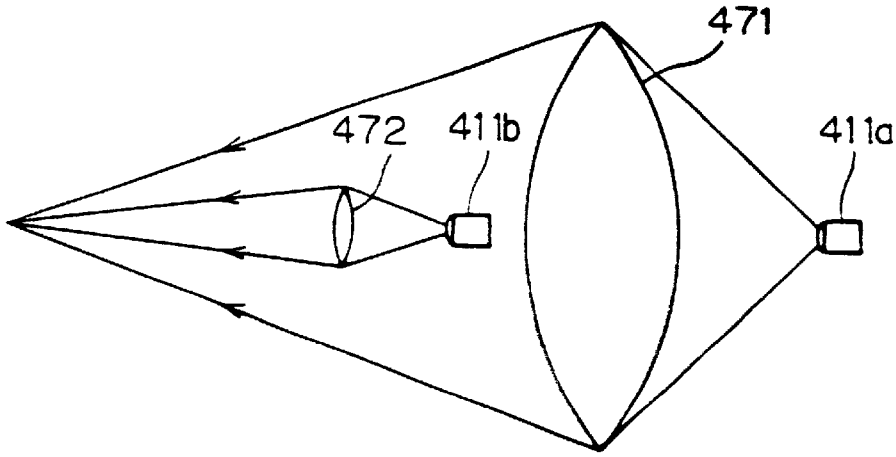
FIGS. 22A, 22B & 22C are diagrams showing a method of guiding light of different wavelengths on the same optical path.
Figure 22B:
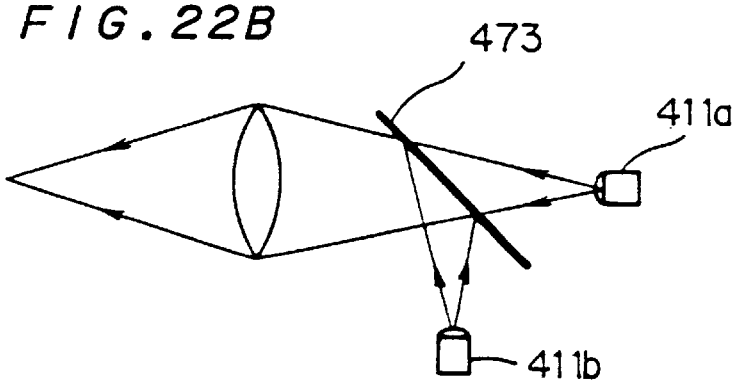
Figure 22C:
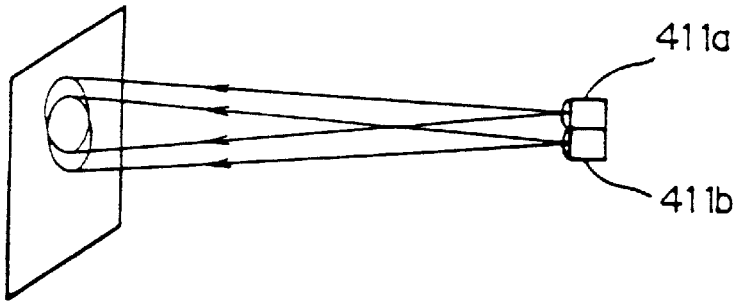

While the aforementioned embodiment guides the light of two different wavelengths onto the same optical path by employing the fiber unit, alternatively, a lens 471 of a large aperture and a lens 472 of a small aperture may be employed light is applied from the lens 471 behind the lens 472 and guided onto the same optical path as light from the lens 472 of a small aperture, as shown in FIG. 22A. Or, light of two different wavelengths may be guided onto the same optical path through a half mirror 473, as shown in FIG. 22B. Or, it is also possible to arrange two light-emitting devices 411a and 411b in close proximity for guiding light from these light-emitting devices onto a substantially identical optical path by diverging the same.

Further, detection becomes possible over a wide range by making light of two different wavelengths guided on the same optical path raster-scanned through a polygon mirror or the like.

While the respective embodiments of the present invention have been described, the scope of the present invention is not restricted to the aforementioned embodiments, but is defined by the scope of attached claims.

We claim:

1. A device which determines whether a substance contains an OH [groups] *group,* said device comprising:

a semiconductor [light emitting device] *laser* which generates light having a wavelength between 1.40 $\mu$m to 1.50 $\mu$m, said light being applied to a substance;

a photoreceptor responsive to light which originated from said semiconductor [light emitting device] *laser* and is received from said substance, said photoreceptor generating an output as a function thereof; and a comparator which compares said output with a threshold value and generates a detection signal in response to the comparison, said detection signal indicating whether said substance contains an OH group.

2. The device in accordance with claim 1, further comprising:

a first optical guide which guides light from said semiconductor [light emitting device] *laser* to said substance, and a second optical guide which guides light from said substance to said photoreceptor.

3. The [switching] device in accordance with claim 1, further comprising:

a controller which is effective to change said [prescribed] threshold value.

4. A device which determines whether a substance contains a $CH_2$ or $CH_3$ group, said device comprising:

a semiconductor [light emitting device] *laser* which generates light having a wavelength between 1.60 $\mu$m to 1.80 $\mu$m, said light being applied to a substance;

a photoreceptor responsive to light which originated from said semiconductor [light emitting device] *laser* and is received from said substance, said photoreceptor generating an output as a function thereof; and a comparator which compares said output with a threshold value and generates a detection signal in response to the comparison said detection signal indicating whether said substance contains a $CH_2$ group or a $CH_3$ group.

5. The device in accordance with claim 4, further comprising:

a first optical guide which guides light from said semiconductor [light emitting device] *laser* to said substance, and a second optical guide which guides light from said substance to said photoreceptor.

6. The [photoelectric switching] device in accordance with claim 4, further comprising:

a controller which is effective to [chance] *change* said threshold value.

7. A device which detects the existence of a substance, *disposed within or upon an object, said substance* containing an OH group, a $CH_2$ group, or a $CH_3$ group and producing a detection signal in response thereto, said device comprising:

a first light source in the form of a semiconductor light emitting element which generates a first light having a first wavelength between 1.40 $\mu$m to 1.50 $\mu$m or between 1.60 $\mu$m to 1.80 $\mu$m, said first light being applied to [said substance] *an object*;

a second light source which generates a second light of a second wavelength different from said first wavelength, said second light being applied to said substance;

a photoreceptor responsive to light which originated from said first and second light sources and is received from said substance, said photoreceptor generating first and second outputs in response to receiving said light from said first and second light sources; and a signal generator which generates said detection signal in response to said first and second outputs, said signal generator having a first comparator which compares said second output with a conditional threshold value and produces a comparison result in response to the comparison of said first comparator, a first amplifier which modifies said first output in response to said comparison result thereby producing a modified first output, and a second comparator which compares said modified first output with a detection threshold value and generates said detection signal in response to the comparison of said second comparator,

*wherein said first light and second light are affected by a surface state of said object, said first wavelength is included in an absorption band of said substance, and said second wavelength is excluded from said absorption band.*

[8. The photoelectric switching device in accordance with claim 7, wherein said signal generator further comprises:

a third comparator which compares said second output with a second conditional threshold value which is adjustable and produces, in response to the comparison of said third comparator, another comparison result; and a second amplifier which modifies said first output in response to said another comparison result.]

9. The device in accordance with claim 7, wherein said first and second lights of different wavelengths are visible light and invisible light, respectively.

10. The device in accordance with claim 7, wherein said signal generator further comprises:

a controller which is effective to change said detection threshold value.

11. The device in accordance with claim 7, further comprising:

a fiber unit which guides said first and second lights of different wavelengths on a single optical path.

12. The device in accordance with claim 7, wherein said signal generator further comprises:

a controller which is effective to change said conditional threshold value.

13. The device in accordance with claim 7, further comprising:

a light [control] *controller* which controls a turning-on and turning-off said light sources independently.

[14. The device in accordance with claim 9, further comprising:

a third comparator which compares said second output with a gate threshold value and generates a gate signal in response to the comparison of said third comparator, said gate signal indicating a presence of said detection object;

a fourth comparator which compares said first output with a detection threshold value and generates another detection signal in response to the comparison of said fourth comparator; and a gate which combines said another detection signal with said gate signal thereby generating said detection signal.]

15. A method of detecting [the presence of] a substance containing an OH group, said method comprising:

applying light having a wavelength between 1.40 $\mu$m to 1.50 $\mu$m from a semiconductor [light emitting device] *laser* toward a substance;

generating an output responsive to light originating from said semiconductor [light emitting device] *laser* and received from said substance; and comparing said output with a prescribed threshold value and generating a detection signal indicating whether said substance contains an OH group.

16. A method of detecting a substance containing a $CH_2$ group or a $CH_3$ group, said method comprising:

applying light of a wavelength between 1.60 $\mu$m to 1.80 $\mu$m from a semiconductor [light emitting device] *laser* toward a substance;

generating an output responsive to light originating from said semiconductor [light emitting device] *laser* and received from said substance; and comparing said output with a prescribed threshold value and generating a detection signal indicating whether said substance contains a $CH_2$ group or a $CH_3$ group.

17. A method of detecting the existence of a substance, *disposed within or upon an object, said substance* containing [one of] an OH group, a $CH_2$ group, or a $CH_3$ group, said method comprising:

applying first light having a first wavelength between 1.40 $\mu$m to 1.50 $\mu$m or between 1.60 $\mu$m to 1.80 $\mu$m toward a substance, said first light being generated by a semiconductor light emitting device;

applying second light of a second wavelength different from said first wavelength toward said substance, said second light being generated by a second light source;

generating first and second outputs responsive to light originating from said light sources and received from said substance;

first comparing said second output with a conditional threshold value and producing a comparison result in response to said first comparing;

modifying said first output in response to said comparison result, thereby producing a modified first output; and second comparing said modified first output with a detection threshold value and generating, in response to said second comparing, said detection signal which indicates the existence of a substance containing one of an OH group, a $CH_2$ group, or a $CH_3$ group,

*wherein said first light and second light are affected by a surface state of said object, said first wavelength is included in an absorption band of said substance, and a second wavelength is excluded from said absorption band.*

18. The method in accordance with claim 17, further comprising:

pre-applying said first and second light upon an adjusting object and adjusting said detection threshold value and said conditional threshold value on the basis of light received from said adjusting object before performing said applying first light and applying second light.

19. The [switching] method in accordance with claim 17, wherein said step of modifying comprises:

multiplying said first output by a prescribed value in response to said second output and said [detection signal] *comparison result*.

[20. The method in accordance with claim 17, further comprising:

third comparing said second output with a gate threshold value and generating a gate signal in response to said third comparing, said gate signal indicating a presence of an object having said substance disposed within or upon said object; and deciding whether or not said detection signal is to be outputted in response to said gate signal.]

21. A device which detects the existence of a substance, disposed within or upon an object, containing one of an OH group, a $CH_2$ group, or a $CH_3$ group, said device comprising:

a first light source in the form of a semiconductor light emitting element which generates a first light having a wavelength between 1.40 $\mu$m to 1.50 $\mu$m or between 1.60 $\mu$m to 1.80 $\mu$m, said first light being applied to a region of said object;

[a second light source which generates visible light being applied to said object, wherein said visible light [indicates] points out said region of said object;]

a second light source which generates visible light being applied to said object, wherein said visible light points out said region of said object;

a photoreceptor responsive to said first light originating from said first light source and received from said substance, said photoreceptor generating an output which is a function of said first light; and a signal generator which generates a detection signal in response to said output, indicating whether said substance contains one of an OH group, a $CH_2$ group, or a $CH_3$ group.

22. A device which detects the existence of a substance, *disposed within or upon an object, said substance* having [one of] an OH group, a $CH_2$ group, or a $CH_3$ group, said device comprising:

at least a first light source in the form of a semiconductor [light emitting device] *laser* and which emanates a first light toward said [substance] *object*, said first light having a first wavelength, said first wavelength being selected so that [one of a reflection and an] absorption of said first light is affected by whether said substance contains [one of] an OH group, a $CH_2$ group, or a $CH_3$ group;

a photoreceptor disposed so as to receive received light which originated from said first light source, said received light being received from said [substance] *object*; and a controller which analyzes characteristics of said received light which was received by said photoreceptor and determines said existence of a substance having [one of] an OH group, a $CH_2$ group, or a $CH_3$ group.

23. The device as claimed in claim 22 further comprising:

[an object having said substance disposed within or upon said object; and]

at least a second light source which emanates a second light toward said substance, said second light having a second wavelength, said second wavelength being selected so that [one of a] reflection [and an absorption] of said second light is affected by a surface state of said object;

wherein said photoreceptor is responsive to light which originated from said second light source and is received from said [substance] *object*.

24. A method of detecting the existence of a substance, *disposed within or upon an object, said substance having* [containing one of] an OH group, a $CH_2$ group, or a $CH_3$ group, said method comprising:

applying to said [substance] *object* a first light having a first wavelength and originating from a semiconductor [light emitting device] *laser*, said first wavelength being selected so that [one of a reflection and an] absorption of said first light is affected by whether said substance contains [one of] an OH group, a $CH_2$ group and a $Ch_3$ group;

receiving received light which originated from said first light and which has been received from said [substance] *object*; and analyzing characteristics of said received light to determine whether said substance contains [one of] an OH group, a $CH_2$ group or a $CH_3$ group.

25. The method as claimed in claim 24 further comprising:

applying to [an] *said* object a second light having a second wavelength, said second wavelength being selected so that [one of a] reflection [and an absorption] of said second light is affected by a surface state of [an] *said* object[, said object having said substance disposed within or upon said object].

* * * * *